United States Patent
Eggers et al.

(10) Patent No.: US 6,179,836 B1
(45) Date of Patent: *Jan. 30, 2001

(54) PLANAR ABLATION PROBE FOR ELECTROSURGICAL CUTTING AND ABLATION

(75) Inventors: Philip E. Eggers, Dublin, OH (US); Hira V. Thapliyal, Los Altos, CA (US)

(73) Assignee: ArthroCare Corporation, Sunnyvale, CA (US)

( * ) Notice: Under 35 U.S.C. 154(b), the term of this patent shall be extended for 0 days.

This patent is subject to a terminal disclaimer.

(21) Appl. No.: 09/181,936

(22) Filed: Oct. 28, 1998

Related U.S. Application Data

(60) Division of application No. 08/690,159, filed on Jul. 18, 1996, now Pat. No. 5,902,272, which is a continuation-in-part of application No. 08/561,958, filed on Nov. 22, 1996, now Pat. No. 5,697,882, which is a continuation-in-part of application No. 08/485,219, filed on Jun. 7, 1995, now Pat. No. 5,697,281, which is a continuation-in-part of application No. PCT/US94/05168, filed on May 10, 1994, which is a continuation-in-part of application No. 08/059,681, filed on May 10, 1993, now abandoned, which is a continuation-in-part of application No. 07/958,977, filed on Oct. 9, 1992, now Pat. No. 5,366,443, which is a continuation-in-part of application No. 07/817,575, filed on Jan. 7, 1992, now abandoned.

(51) Int. Cl.$^7$ .................................................. A61B 18/18
(52) U.S. Cl. ............................... 606/45; 606/41; 607/105
(58) Field of Search ................................. 606/41, 42, 45, 606/48–50; 600/372, 374; 607/101, 102, 115, 116, 117, 104, 105

(56) References Cited

U.S. PATENT DOCUMENTS 2,050,904  8/1936  Trice .
4,040,426  8/1977  Morrison, Jr. .
4,043,342  8/1977  Morrison, Jr. .
4,092,986  6/1978  Schneiderman .
4,116,198  9/1978  Roos .
4,184,492  1/1980  Meinke et al. .
4,202,337  5/1980  Hren et al. .

(List continued on next page.)

FOREIGN PATENT DOCUMENTS 515 867    12/1992  (EP) .
0 703 461   3/1996  (EP) .
0 740 926  11/1996  (EP) .
0 754 437   1/1997  (EP) .

(List continued on next page.)

OTHER PUBLICATIONS

C. Slager et al. (1985) *JACC* 5(6):1382–6.
C. Slager et al. (1987) *Z. Kardiologie* 76(6):67–71.
J. Saal et al. NASS–APS First Joint Meeting, Charleston SC, Apr. 1998.

(List continued on next page.)

*Primary Examiner*—Michael Peffley
(74) *Attorney, Agent, or Firm*—John T. Raffle

(57) ABSTRACT

An electrosurgical ablation probe is provided having a shaft with a proximal end portion and a tongue-shaped distal end portion sized to fit within confined (e.g., narrow) spaces within the patient's body, such as the spaces around the articular cartilage between the femur and tibia and the spaces between adjacent vertebrae in the patient's spine. The probe includes at least one active electrode integral with or coupled to the tongue-shaped distal end portion and a connector on the proximal end portion for coupling the active electrode to an electrosurgical generator. The tongue-shaped distal end portion is substantially planar, and it offers a low profile, to allow access to confined spaces without risking iatrogenic injury to surrounding tissue, such as articular cartilage.

18 Claims, 33 Drawing Sheets

U.S. PATENT DOCUMENTS

| | | |
|---|---|---|
| 4,228,800 | 10/1980 | Degler, Jr. et al. . |
| 4,232,676 | 11/1980 | Herczog . |
| 4,240,441 | 12/1980 | Khalil . |
| 4,248,231 | 2/1981 | Herczog et al. . |
| 4,326,529 | 4/1982 | Doss et al. . |
| 4,381,007 | 4/1983 | Doss . |
| 4,476,862 | 10/1984 | Pao . |
| 4,532,924 | 8/1985 | Auth et al. . |
| 4,548,207 | 10/1985 | Reimels . |
| 4,567,890 | 2/1986 | Ohta et al. . |
| 4,593,691 | 6/1986 | Lindstrom et al. . |
| 4,658,817 | 4/1987 | Hardy . |
| 4,674,499 | 6/1987 | Pao . |
| 4,682,596 | 7/1987 | Bales et al. . |
| 4,706,667 | 11/1987 | Roos . |
| 4,765,331 | 8/1988 | Petruzzi et al. . |
| 4,813,429 | 3/1989 | Eshel et al. . |
| 4,823,791 | 4/1989 | D'Amelio et al. . |
| 4,860,752 | 8/1989 | Turner . |
| 4,896,671 | 1/1990 | Cunningham et al. . |
| 4,931,047 | 6/1990 | Broadwin et al. . |
| 4,936,301 | 6/1990 | Rexroth et al. . |
| 4,943,290 | 7/1990 | Rexroth et al. . |
| 4,967,765 | 11/1990 | Turner et al. . |
| 4,976,711 | 12/1990 | Parins et al. . |
| 4,979,948 | 12/1990 | Geddes et al. . |
| 4,998,933 | 3/1991 | Eggers et al. . |
| 5,007,908 | 4/1991 | Rydell . |
| 5,009,656 | 4/1991 | Reimels . |
| 5,035,696 | 7/1991 | Rydell . |
| 5,057,105 | 10/1991 | Malone et al. . |
| 5,057,106 | 10/1991 | Kasevich et al. . |
| 5,078,717 | 1/1992 | Parins et al. . |
| 5,080,660 * | 1/1992 | Buelna ................... 606/45 |
| 5,083,565 | 1/1992 | Parins . |
| 5,098,431 | 3/1992 | Rydell . |
| 5,108,391 | 4/1992 | Flachenecker . |
| 5,112,330 | 5/1992 | Nishigaki et al. . |
| 5,122,138 | 6/1992 | Manwaring . |
| 5,125,928 | 6/1992 | Parins et al. . |
| 5,176,528 | 1/1993 | Fry et al. . |
| 5,178,620 | 1/1993 | Eggers et al. . |
| 5,190,517 | 3/1993 | Zieve et al. . |
| 5,192,280 | 3/1993 | Parins . |
| 5,195,959 | 3/1993 | Smith . |
| 5,197,963 | 3/1993 | Parins . |
| 5,201,729 | 4/1993 | Hertzmann et al. . |
| 5,217,457 | 6/1993 | Delahuerga et al. . |
| 5,249,585 | 10/1993 | Turner et al. . |
| 5,267,994 | 12/1993 | Gentelia et al. . |
| 5,267,997 | 12/1993 | Farin et al. . |
| 5,273,524 | 12/1993 | Fox et al. . |
| 5,277,201 | 1/1994 | Stern . |
| 5,281,216 | 1/1994 | Klicek . |
| 5,281,218 | 1/1994 | Imran . |
| 5,290,282 | 3/1994 | Casscells . |
| 5,300,069 | 4/1994 | Hunsberger et al. . |
| 5,312,400 | 5/1994 | Bales et al. . |
| 5,314,406 | 5/1994 | Arias et al. . |
| 5,324,254 | 6/1994 | Phillips et al. . |
| 5,330,470 | 7/1994 | Hagen . |
| 5,334,140 | 8/1994 | Phillips . |
| 5,334,183 | 8/1994 | Wuchinich . |
| 5,336,220 | 8/1994 | Ryan et al. . |
| 5,342,357 | 8/1994 | Nardella . |
| 5,366,443 | 11/1994 | Eggers et al. . |
| 5,370,675 | 12/1994 | Edwards et al. . |
| 5,380,277 | 1/1995 | Phillips . |
| 5,383,876 | 1/1995 | Nardella . |
| 5,383,917 | 1/1995 | Desai et al. . |
| 5,395,312 | 3/1995 | Desai . |
| 5,403,311 * | 4/1995 | Abele et al. ............ 606/50 |
| 5,417,687 | 5/1995 | Nardella et al. . |
| 5,419,767 | 5/1995 | Eggers et al. . |
| 5,433,739 | 7/1995 | Sluijter et al. . |
| 5,439,446 | 8/1995 | Barry . |
| 5,441,499 | 8/1995 | Fritzsch . |
| 5,454,809 | 10/1995 | Janssen . |
| 5,458,596 * | 10/1995 | Lax et al. ............... 606/31 |
| 5,514,130 | 5/1996 | Baker . |
| 5,542,945 * | 8/1996 | Fritzsch ................ 606/48 |
| 5,556,397 | 9/1996 | Long et al. . |
| 5,562,703 | 10/1996 | Desai . |
| 5,569,242 | 10/1996 | Lax et al. . |
| 5,609,151 | 3/1997 | Mulier et al. . |
| 5,647,869 | 7/1997 | Goble et al. . |
| 5,662,680 | 9/1997 | Desai . |
| 5,681,282 * | 10/1997 | Eggers et al. ............ 604/114 |
| 5,683,366 | 11/1997 | Eggers et al. . |
| 5,697,281 | 12/1997 | Eggers et al. . |
| 5,697,536 | 12/1997 | Eggers et al. . |
| 5,697,882 | 12/1997 | Eggers et al. . |
| 5,697,909 | 12/1997 | Eggers et al. . |
| 5,700,262 | 12/1997 | Acosta . |
| 5,720,744 | 2/1998 | Eggleston et al. . |
| 5,725,524 | 3/1998 | Mulier et al. . |
| 5,749,869 | 5/1998 | Lindenmeier . |
| 5,766,153 | 6/1998 | Eggers et al. . |
| 5,807,395 | 9/1998 | Mulier et al. . |
| 5,810,764 | 9/1998 | Eggers et al. . |
| 5,846,196 * | 12/1998 | Siekmeyer ................ 600/374 |
| 5,849,009 * | 12/1998 | Bernaz .................. 606/36 |
| 5,860,975 * | 1/1999 | Goble et al. ............. 606/45 |
| 5,885,277 | 3/1999 | Korth . |
| 5,897,553 | 4/1999 | Mulier et al. . |
| 5,944,715 | 8/1999 | Goble et al. . |
| 5,954,716 | 9/1999 | Sharkey et al. . |
| 6,004,319 | 12/1999 | Goble et al. . |
| 6,007,570 | 12/1999 | Sharkey et al. . |
| 6,013,076 | 1/2000 | Goble et al. . |
| 6,015,406 | 1/2000 | Goble et al. . |
| 6,027,501 | 2/2000 | Goble et al. . |
| 6,039,734 | 3/2000 | Goble et al. . |
| 6,056,746 | 5/2000 | Goble et al. . |
| 6,068,628 | 5/2000 | Fanton et al. . |
| 6,073,051 | 6/2000 | Sharkey et al. . |
| 6,074,386 | 6/2000 | Goble et al. . |
| 6,090,106 | 7/2000 | Goble et al. . |
| 6,093,186 | 7/2000 | Goble et al. . |

FOREIGN PATENT DOCUMENTS

| | | |
|---|---|---|
| 2 308 979 | 7/1997 | (GB) . |
| 2 308 980 | 7/1997 | (GB) . |
| 2 308 981 | 7/1997 | (GB) . |
| 57-117843 | 7/1982 | (JP) . |
| WO 90/07303 | 7/1990 | (WO) . |
| WO 92/21278 | 12/1992 | (WO) . |
| WO 93/13816 | 7/1993 | (WO) . |
| WO 93/20747 | 10/1993 | (WO) . |
| WO 94/04220 | 3/1994 | (WO) . |
| 94/08654 | 4/1994 | (WO) . |
| WO 94/14383 | 7/1994 | (WO) . |
| WO 94/26228 | 11/1994 | (WO) . |
| WO 95/34259 | 12/1995 | (WO) . |
| 96/00042 | 1/1996 | (WO) .............. A61B/17/39 |
| 96/23449 | 8/1996 | (WO) .............. A61B/17/39 |
| WO 96/23449 | 8/1996 | (WO) . |
| 96/41574 | 12/1996 | (WO) .............. A61B/17/04 |
| WO 97/00646 | 1/1997 | (WO) . |
| WO 97/00647 | 1/1997 | (WO) . |
| 97/24073 | 7/1997 | (WO) . |

| | | |
|---|---|---|
| 97/24992 | 7/1997 | (WO). |
| 97/24993 | 7/1997 | (WO). |
| 97/24994 | 7/1997 | (WO). |
| 97/48346 | 12/1997 | (WO). |
| 98/00070 | 1/1998 | (WO) .............................. A61B/17/36 |
| 98/07468 | 2/1998 | (WO). |
| 98/11944 | 3/1998 | (WO). |
| 98/17190 | 4/1998 | (WO). |
| 98/27879 | 7/1998 | (WO). |
| 99/47058 | 9/1999 | (WO). |
| 99/51155 | 10/1999 | (WO). |
| 99/51158 | 10/1999 | (WO). |

OTHER PUBLICATIONS

V.E. Elsasser et al. *Acta Medicotechnica* 24(4):129–134 (1976).

M. Buchelt et al. *Lasers In Surgery and Medecine* 11:271–279 (1991).

J. Costello *Lasers in Surgery and Medecine* 12:121–124 (1992).

Rand et al. (1985) *J. Arthro. Surg.* 1:242–246 Effect of Electrocautery on Fresh Human Articular Cartilage.

R. Tucker et al., Abstract P14–11, p. 248, "A Bipolar Electrosurgical Turp Loop".

R. Tucker et al. *J. of Urology* vol. 141, pp. 662–665, (1989).

R. Tucker et al. *Urological Research* vol. 18, pp. 291–294 (1990).

E.V. Kramolowsky et al. *J. of Urology* vol. 143, pp. 275–277 (1990).

J.W. Ramsey et al. *Urological Research* vol. 13, pp. 99–102 (1985).

P.C. Nardella (1989) *SPIE* 1068:42–49 Radio Frequency Energy and Impedance Feedback.

E. Kramolowsky et al. (1991) *J. of Urology* 146:669–674. The Urological Application of Electrosurgery.

* cited by examiner

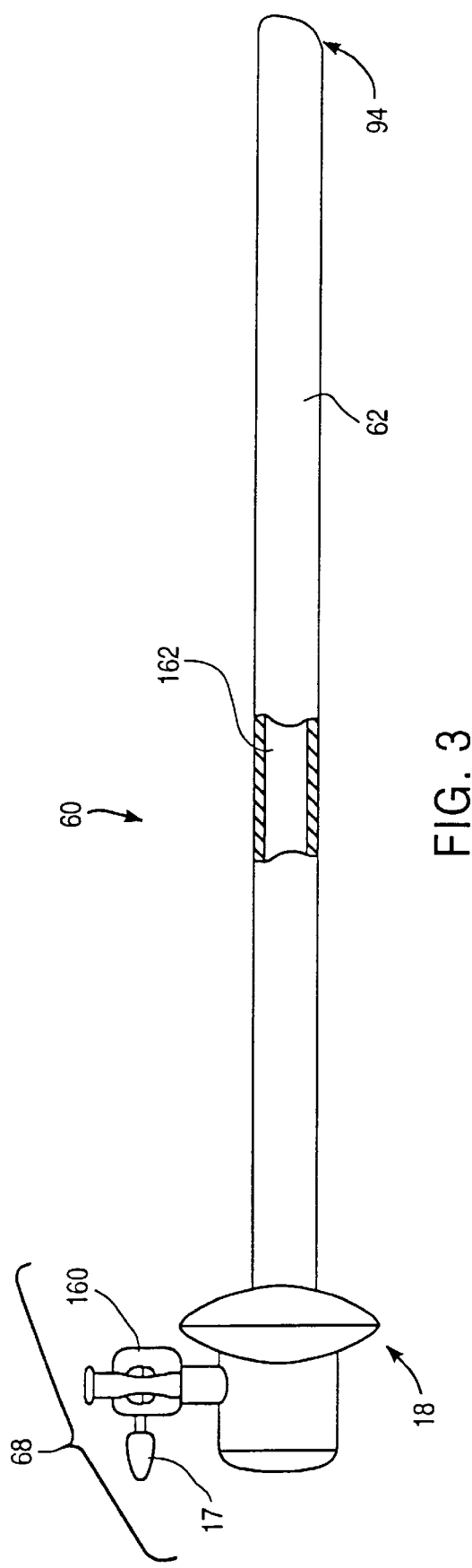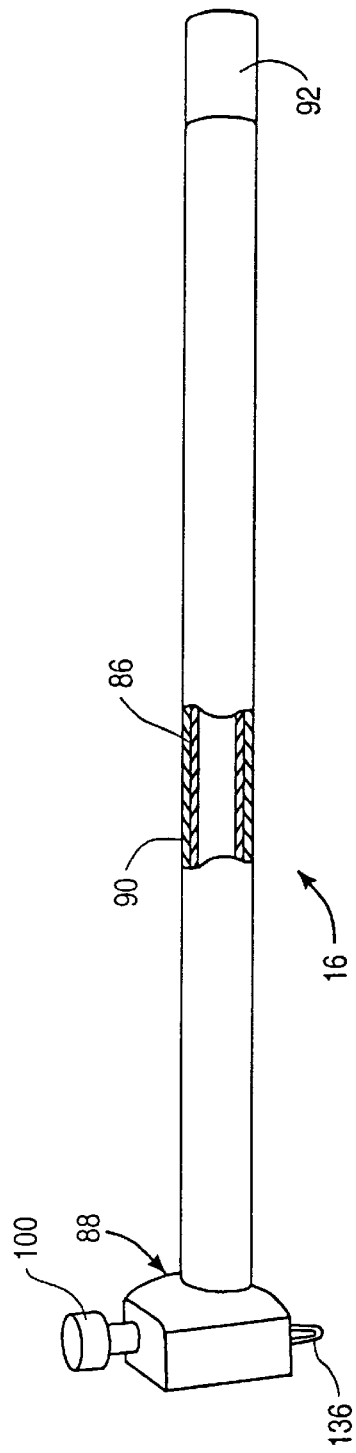
FIG. 3
FIG. 4

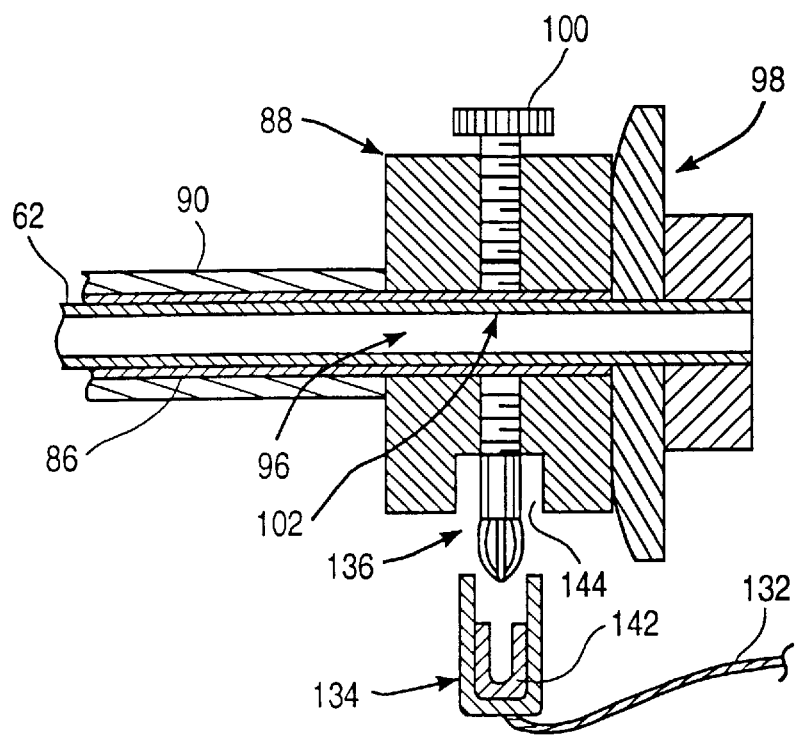
FIG. 5
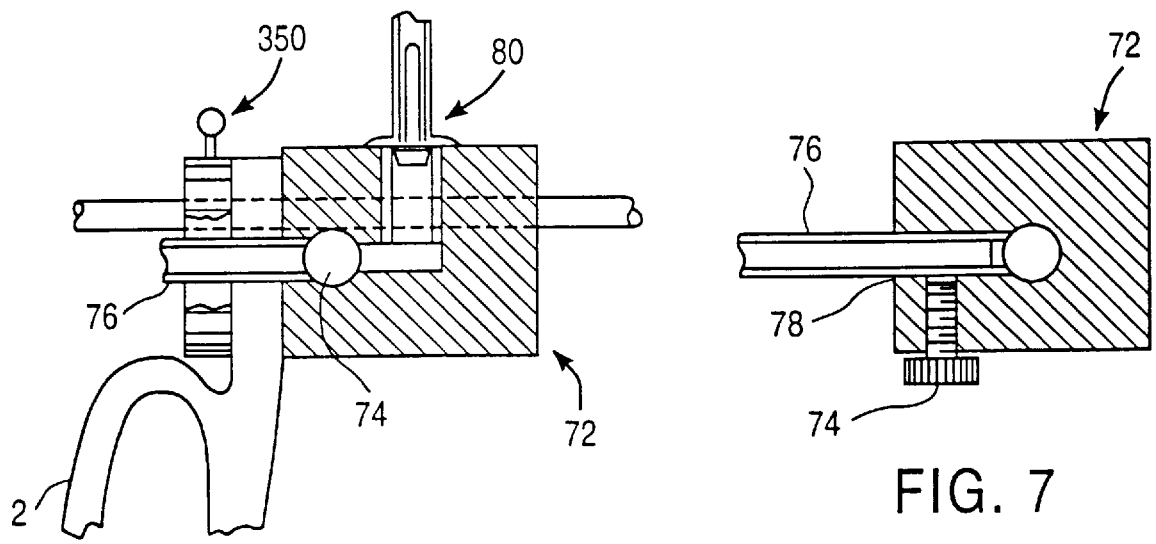
FIG. 6
FIG. 7

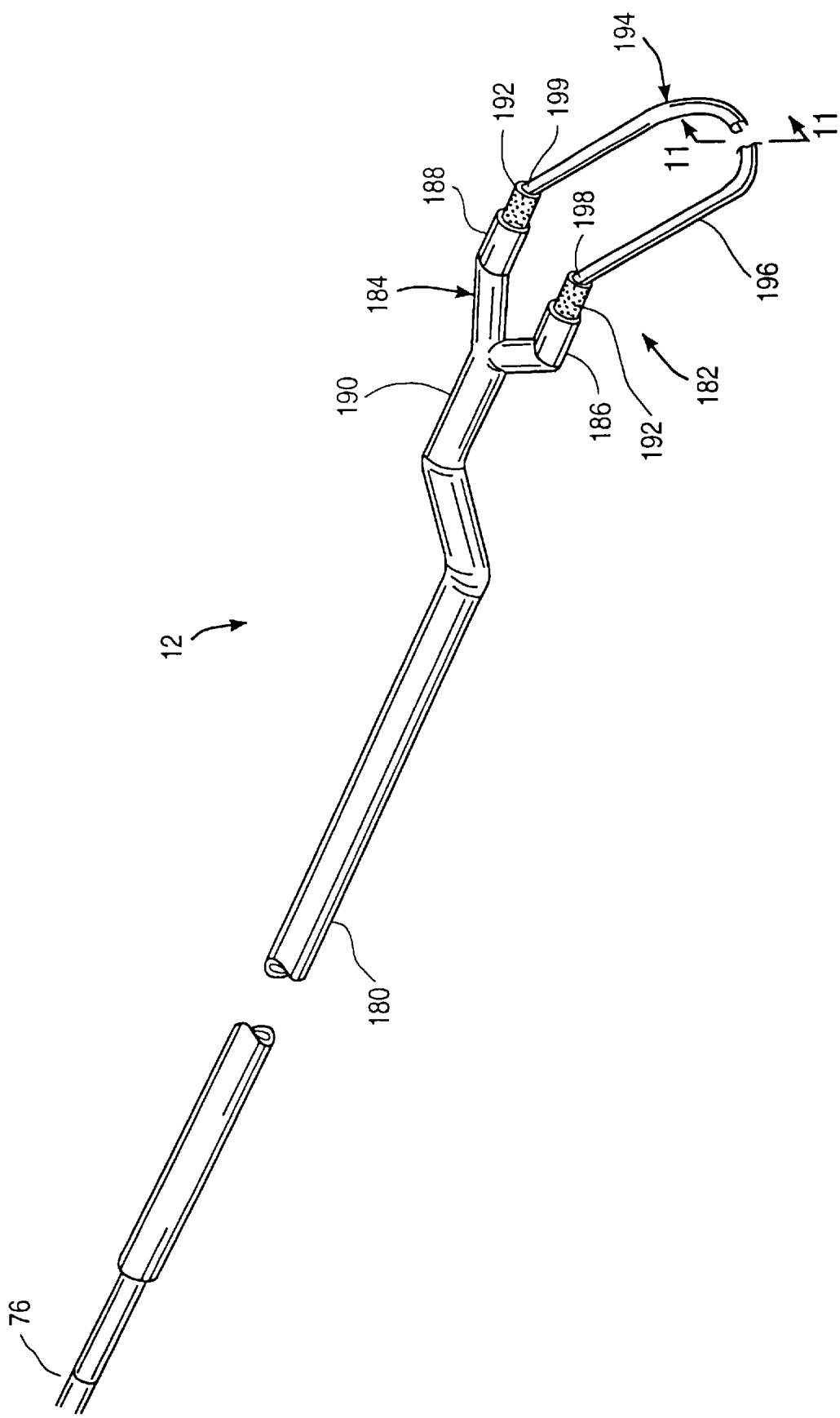

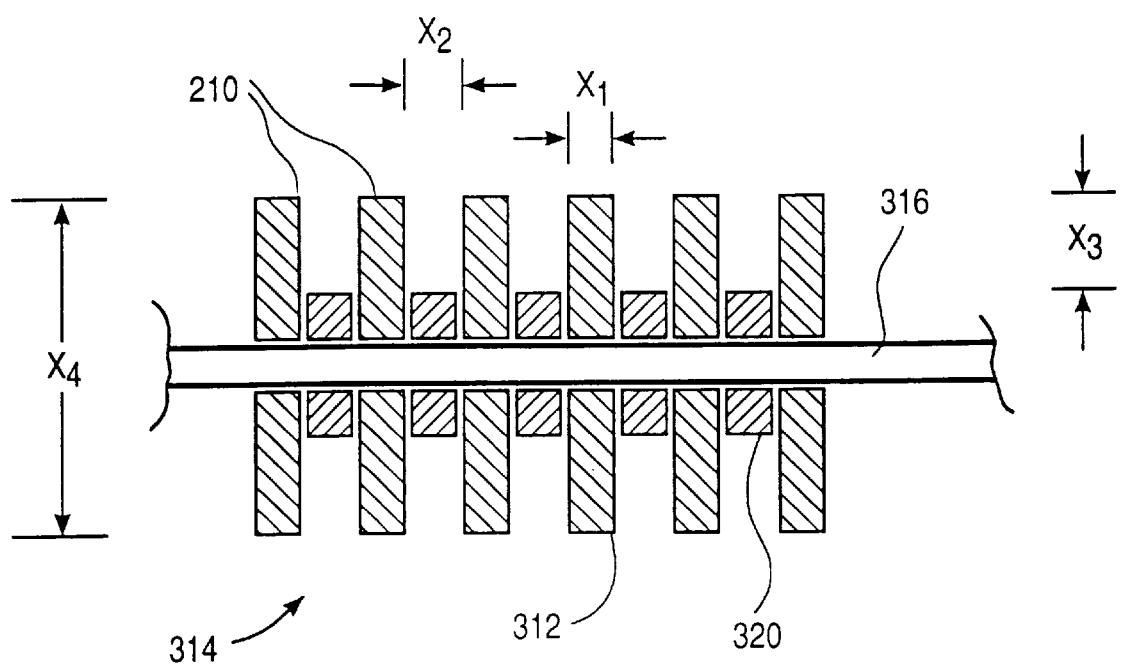
FIG. 19
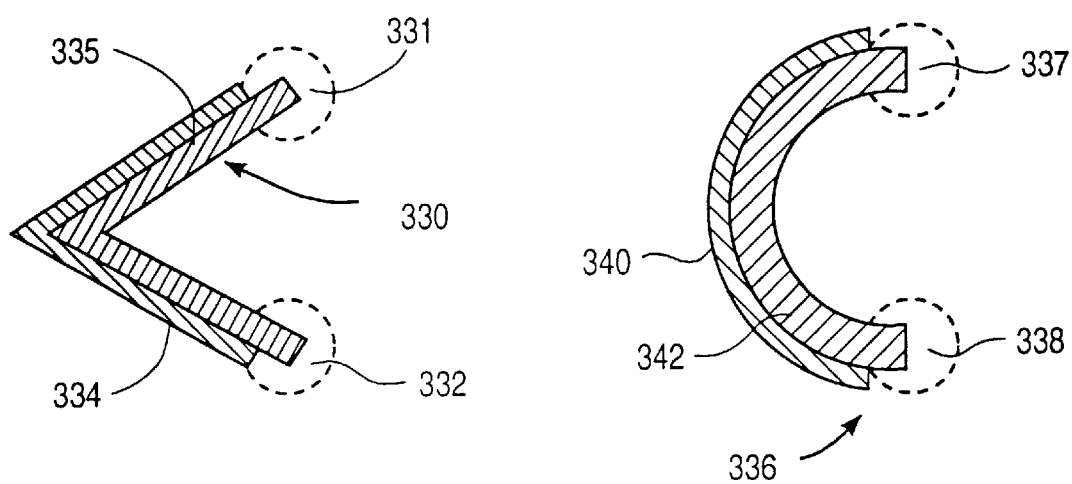
FIG. 20A
FIG. 20B

PLANAR ABLATION PROBE FOR ELECTROSURGICAL CUTTING AND ABLATION

CROSS-REFERENCE TO RELATED APPLICATIONS

This application is a continuation division of and a continuation-in-part of application Ser. No. 08/561,958, filed on Nov. 22, 1996, now U.S. Pat. No. 5,697,882, which was a continuation-in-part of Ser. No. 08/485,219, filed on Jun. 7, 1995, now U.S. Pat. No. 5,697,281, which was a continuation-in-part of PCT International Application, U.S. National Phase Ser. No. PCT/US94/05168, filed on May 10, 1994, which was a continuation-in-part of application Ser. No. 08/059,681, filed on May 10, 1993 (now abandoned), which was a continuation-in-part of application Ser. No. 07/958,977, filed on Oct. 9, 1992, now U.S. Pat. No. 5,366,443, which was a continuation-in-part of application Ser. No. 07/817,575, filed on Jan. 7, 1992 (now abandoned), the full disclosures of which are incorporated herein by reference.

BACKGROUND OF THE INVENTION

1. Field of the Invention

The present invention relates generally to the field of electrosurgery and, more particularly, to surgical devices and methods which employ high frequency voltage to cut and ablate tissue.

The field of electrosurgery includes a number of loosely related surgical techniques which have in common the application of electrical energy to modify the structure or integrity of patient tissue. Electrosurgical procedures usually operate through the application of very high frequency currents to cut or ablate tissue structures, where the operation can be monopolar or bipolar. Monopolar techniques rely on external grounding of the patient, where the surgical device defines only a single electrode pole. Bipolar devices comprise both electrodes for the application of current between their surfaces.

Electrosurgical procedures and techniques are particularly advantageous since they generally reduce patient bleeding and trauma associated with cutting operations. Current electrosurgical devices and procedures, however, suffer from a number of disadvantages. For example, monopolar devices generally direct electric current along a defined path from the exposed or active electrode through the patient's body to the return electrode, which is externally attached to a suitable location on the patient. This creates the potential danger that the electric current will flow through undefined paths in the patient's body, thereby increasing the risk of unwanted electrical stimulation to portions of the patient's body. In addition, since the defined path through the patient's body has a relatively high impedance (because of the large distance or resistivity of the patient's body), large voltage differences must typically be applied between the return and active electrodes in order to generate a current suitable for ablation or cutting of the target tissue. This current, however, may inadvertently flow along body paths having less impedance than the defined electrical path, which will substantially increase the current flowing through these paths, possibly causing damage to or destroying tissue along and surrounding this pathway.

Bipolar electrosurgical devices have an inherent advantage over monopolar devices because the return current path does not flow through the patient. In bipolar electrosurgical devices, both the active and return electrode are typically exposed so that they may both contact tissue, thereby providing a return current path from the active to the return electrode through the tissue. One drawback with this configuration, however, is that the return electrode may cause tissue desiccation or destruction at its contact point with the patient's tissue. In addition, the active and return electrodes are typically positioned close together to ensure that the return current flows directly from the active to the return electrode. The close proximity of these electrodes generates the danger that the current will short across the electrodes, possibly impairing the electrical control system and/or damaging or destroying surrounding tissue.

The use of electrosurgical procedures (both monopolar and bipolar) in electrically conductive environments can be further problematic. For example, many arthroscopic procedures require flushing of the region to be treated with isotonic saline (also referred to as normal saline), both to maintain an isotonic environment and to keep the field of viewing clear. The presence of saline, which is a highly conductive electrolyte, can also cause shorting of the electrosurgical electrode in both monopolar and bipolar modes. Such shorting causes unnecessary heating in the treatment environment and can further cause non-specific tissue destruction.

Present electrosurgical techniques used for tissue ablation also suffer from an inability to control the depth of necrosis in the tissue being treated. Most electrosurgical devices rely on creation of an electric arc between the treating electrode and the tissue being cut or ablated to cause the desired localized heating. Such arcs, however, often create very high temperatures causing a depth of necrosis greater than 500 $\mu$m, frequently greater than 800 $\mu$m, and sometimes as great as 1700 $\mu$m. The inability to control such depth of necrosis is a significant disadvantage in using electrosurgical techniques for tissue ablation, particularly in arthroscopic procedures for ablating and/or reshaping fibrocartilage, articular cartilage, meniscal tissue, and the like.

In an effort to overcome at least some of these limitations of electrosurgery, laser apparatus have been developed for use in arthroscopic and other procedures. Lasers do not suffer from electrical shorting in conductive environments, and certain types of lasers allow for very controlled cutting with limited depth of necrosis. Despite these advantages, laser devices suffer from their own set of deficiencies. In the first place, laser equipment can be very expensive because of the costs associated with the laser light sources. Moreover, those lasers which permit acceptable depths of necrosis (such as eximer lasers, erbium:YAG lasers, and the like) provide a very low volumetric ablation rate, which is a particular disadvantage in cutting and ablation of fibrocartilage, articular cartilage, and meniscal tissue. The holmium:YAG and Nd:YAG lasers provide much higher volumetric ablation rates, but are much less able to control depth of necrosis than are the slower laser devices. The $CO_2$ lasers provide high rate of ablation and low depth of tissue necrosis, but cannot operate in a liquid-filled cavity.

For these and other reasons, improved systems and methods are desired for the electrosurgical ablation and cutting of tissue. These systems and methods should be capable of selectively cutting and ablating tissue, while limiting the depth of necrosis and limiting the damage to tissue adjacent to the treatment site.

2. Description of the Background Art

Devices incorporating radio frequency electrodes for use in electrosurgical and electrocautery techniques are described in Rand et al. (1985) *J. Arthro. Surg.* 1:242–246 and U.S. Pat. Nos. 5,281,216; 4,943,290; 4,936,301; 4,593,691; 4,228,800; and 4,202,337: U.S. Pat. Nos. 4,943,290 and 4,936,301 describe methods for injecting non-conducting liquid over the tip of a monopolar electrosurgical electrode to electrically isolate the electrode, while energized, from a surrounding electrically conducting irrigant. U.S. Pat. Nos. 5,195,959 and 4,674,499 describe monopolar and bipolar electrosurgical devices, respectively, that include a conduit for irrigating the surgical site.

U.S. Pat. No. 5,290,286 describes bipolar electrosurgical instruments including a pair of closely spaced conductive electrodes with distal curves to provide scoop-like excision in tissue. U.S. Pat. No. 5,035,696 describes a bipolar electrosurgical cutting wire for a retrograde sphincterotomy. The bipolar cutting wire may be powered using an electrosurgical generator designed to deliver high levels of output power into bipolar devices operating at low impedances. U.S. Pat. No. 4,034,762 describes a bipolar electrosurgical apparatus that utilizes square waves at output voltage levels of 200 to 400 volts with spikes in the waveform with peak voltage values of about 420 volts. U.S. Pat. Nos. 4,969,885 and 4,092,986 teach the advantages of using substantially constant voltage output electrosurgery generators.

SUMMARY OF THE INVENTION

The present invention provides a system and method for selectively applying electrical energy to structures within or on the surface of a patient's body. The system and method allow the surgical team to perform electrosurgical interventions, such as ablation and cutting of body structures, while limiting the depth of necrosis and limiting damage to tissue adjacent the treatment site. The system and method of the present invention are particularly useful for surgical procedures within accessible sites of the body that are suitable for electrode loop resection, such as the resection of prostate tissue and leiomyomas (fibroids) located within the uterus, and for procedures within confined (e.g., narrow) spaces within the patient's body, such as the spaces around the articular cartilage between the femur and tibia and the spaces between adjacent vertebrae in the patient's spine.

The system according to the present invention comprises an electrosurgical probe having a shaft with a proximal end, a distal end, and at least one active electrode at or near the distal end. A connector is provided at the proximal end of the shaft for electrically coupling the active electrode to a high frequency voltage source. The active electrode includes at least one active portion having a surface geometry configured to promote substantially high electric field intensities and associated current densities between the active portion and the target site when a high frequency voltage is applied to the electrodes. These high electric field intensities and current densities are sufficient to break down the tissue by processes including molecular dissociation or disintegration. The high frequency voltage imparts energy to the target site to ablate a thin layer of tissue without causing substantial tissue necrosis beyond the boundary of the thin layer of tissue ablated. This ablative process can be precisely controlled to effect the volumetric removal of tissue as thin as a few layers of cells with minimal heating of or damage to surrounding or underlying tissue structures.

In an exemplary embodiment, the high electric field intensities at the active portion of the active electrode may be generated by positioning the active electrode and target site within an electrically conducting liquid, such as isotonic saline, and applying a high frequency voltage that is sufficient to vaporize the electrically conducting liquid over at least a portion of the active electrode in the region between the active portion of the active electrode and the target tissue. Since the vapor layer or vaporized region has a relatively high electrical impedance, it increases the voltage differential between the active electrode tip and the tissue and causes ionization within the vapor layer due to the presence of an ionizable species (e.g., sodium when isotonic saline is the electrically conducting fluid). This ionization, under optimal conditions, induces the discharge of energetic electrons and photons from the vapor layer and to the surface of the target tissue. A more detailed description of this phenomena can be found in application Ser. No. 08/561,958, filed on Nov. 22, 1996 (Attorney Docket 16238-000700), the complete disclosure of which has already been incorporated herein by reference.

Suitable electrode surface geometries for producing sufficiently high electric field intensities to reach the threshold conditions for vapor layer formation may be obtained by producing sharp edges and/or corners at the active portion of the active electrode(s). Alternatively, the electrode(s) may be specifically designed to increase the edge/surface area ratio of the active portion. Electrode shapes according to the present invention can include the use of formed wire (e.g., by drawing round wire through a shaping die) to form electrodes with a variety of cross-sectional shapes, such as square, rectangular, L or V shaped, or the like. Electrode edges may also be created by removing a portion of the elongate metal electrode to reshape the cross-section. For example, material can be removed along the length of a solid or hollow wire electrode to form D or C shaped wires, respectively, with edges facing in the cutting direction. Alternatively, material can be removed at closely spaced intervals along the electrode length to form transverse grooves, slots, threads or the like along the electrodes.

Additionally or alternatively, the active electrode surface (s) may be modified through chemical, electrochemical or abrasive methods to create a multiplicity of surface asperities on the electrode surface. The asperities on the surface of the active electrode(s) promote localized high current densities which, in turn, promote bubble nucleation at the site of the asperities whose enclosed density (i.e., vapor density) is below the critical density to initiate ionization breakdown within the bubble. For example, surface asperities may be created by etching the active electrodes with etchants having a PH less than 7.0 or by using a high velocity stream of abrasive particles (e.g., grit blasting) to create asperities on the surface of an elongated electrode.

In a preferred embodiment, the system includes a return electrode spaced proximally from the active electrode. The return electrode may be integral with the shaft of the probe, or it may be separate from the shaft (e.g., on a liquid supply instrument). In an exemplary embodiment, the return electrode defines a liquid pathway for flow of electrically conducting liquid therethrough. The liquid is directed past the surface of the return electrode and over the active electrode to thereby provide a return current flow path between the target tissue site and the return electrode. A more complete description of methods and apparatus for generating a liquid current flow path between the active and returns electrodes can be found in application Ser. No. 08/485,219, filed on Jun. 7, 1995 (Attorney Docket 16238-000600), the complete disclosure of which has previously been incorporated herein by reference.

In another aspect of the invention, the active electrode will also have a "non-active" portion or surface to selectively reduce undesirable current flow from the non-active portion or surface into tissue or surrounding electrically conducting liquids (e.g., isotonic saline, blood or blood/non-conducting irrigant mixtures). Preferably, the "non-active" electrode portion will be coated with an electrically insulating material. This can be accomplished, for example, with plasma deposited coatings of an insulating material, thin-film deposition of an insulating material using evaporative or sputtering techniques (e.g., $SiO_2$ or $Si_3N_4$), dip coating, or by providing an electrically insulating support member to electrically insulate a portion of the external surface of the electrode. The electrically insulated non-active portion of the active electrode(s) allows the surgeon to selectively ablate tissue, while minimizing necrosis or ablation of surrounding non-target tissue or other body structures.

In one representative embodiment, an electrosurgical resecting instrument is provided having a resecting electrode on the distal end of a shaft and coupled to a high frequency voltage source. The resecting electrode is configured to fit within a working end of a resectoscope (discussed below) and to remove small portions of tissue (e.g., chips of tissue). Preferably, the loop electrode has an elongate body with first and second ends disposed near the distal end of the shaft to form a loop electrode for removing tissue portions and for providing visibility through the loop (i.e., with an optical viewing scope positioned within the resectoscope). The loop electrode may have a variety of shapes, e.g., V-shaped, square or the like. Preferably, the loop electrode has a semi-circular-shape to facilitate rapid resection of tissue chips from the target site.

The elongate body of the loop electrode includes an active portion with a surface geometry configured to promote substantially high electric field intensities and associated current densities between the active portion and the target site when a high frequency voltage is applied to the electrode. Preferably, the electric field intensities generated around the active portion of the loop electrode are sufficient to reach the threshold conditions for vapor layer formation between the electrode and the tissue, as discussed above. To that end, the active portion of the loop electrode can be formed with edges, corners, surface asperities or a combination thereof, to maximize the electric field intensities around the active electrode.

In a preferred configuration, the loop electrode will have a semi-cylindrical cross-section formed by, for example, removing material from a round or hollow tube to form two or more edges on one side of the loop electrode. Preferably, the edges will be oriented substantially parallel to the shaft so that they will face the tissue as the shaft is moved axially in the cutting direction. This orientation facilitates formation of the vapor layer between the electrode edges and the tissue. The opposite or non-active side of the electrode may include an insulating layer to selectively reduce undesirable current flow from the non-active portion into tissue or surrounding electrically conducting liquids.

In an exemplary embodiment, the elongate body of the resecting loop electrode lies in a plane that defines an obtuse angle with the shaft. In this way, the resecting loop electrode defines an obtuse angle with the usual cutting direction as the surgeon moves the resecting instrument parallel to the target tissue. Usually, the resecting loop electrode will define an angle of about 110° to 160° with the shaft, and preferably about 120° to 140. This orientation increases the portion of the resecting loop electrode that is in contact with the tissue rather than exposed to electrically conducting liquid. Consequently, it significantly improves the ease of initiating the requisite conditions for formation of the vapor layer to ablate and cut tissue. In addition, this resecting loop electrode orientation increases the duration of electrode contact with tissue, thereby improving hemostasis of the resected tissue.

The resecting loop instrument of the present invention will usually include a return electrode for completing the current path between the active electrode and the tissue site. The return electrode may be formed on the shaft of the resecting loop electrode, on the resectoscope, or in a separate instrument. In a preferred configuration, the return electrode is formed on a separate return electrode oversheath that includes an electrically conducting hollow tube sized to receive the resecting loop shaft so that the active loop electrode extends beyond the distal end of the hollow tube. The return electrode tube is insulated on its inner and outer surfaces except for an exposed portion that is spaced proximally from the active electrode to generate a current flow path therebetween. The return electrode oversheath may include a liquid path for allowing electrically conducting liquid to flow over the exposed portion to facilitate the formation of the current flow path.

In an alternative embodiment of the resecting loop instrument, the return electrode sheath is insulated on its inner and outer surfaces except for an exposed portion that extends beyond (i.e., overhangs) the distal end of the sheath. The exposed portion generates a current flow path between the resecting loop electrode and the return electrode. If the return electrode is used in conjunction with and positioned over an insulated resecting loop shaft, the return electrode oversheath will be insulated on its outer surface only.

In an exemplary embodiment, the return electrode oversheath includes a proximal hub for connecting the oversheath to a conventional or specialized resectoscope, such as those commercially available from Circon/ACMI of Stamford, Conn. (under the tradename of "USA Elite System Resectoscope") and Olympus Corporation of Lake Success, N.Y. (under the tradename of "OES Resectoscope", Model No. A-2012). In this configuration, the return electrode tube is sized to receive the resectoscope shaft, which usually includes a viewing lumen to provide viewing of the surgical site. The proximal hub will also include a suitable electrical connector for electrically coupling the return electrode to an electrosurgical generator.

In another representative embodiment, an electrosurgical ablation probe is provided having a shaft with a proximal end portion and a tongue-shaped distal end portion sized to fit within confined (e.g., narrow) spaces within the patient's body, such as the spaces around the articular cartilage between the femur and tibia and the spaces between adjacent vertebrae in the patient's spine. The probe includes at least one active electrode integral with or coupled to the tongue-shaped distal end portion and a connector on the proximal end portion for coupling the active electrode to an electrosurgical generator. The tongue-shaped distal end portion is substantially planar, and it offers a low profile, to allow access to confined spaces without risking iatrogenic injury to surrounding tissue, such as articular cartilage. Usually, the distal end portion will have a combined height (i.e., including the active electrode(s)) of less than 2 mm and preferably less than 1 mm.

In a specific configuration, the distal end portion of the probe has an active side and a substantially planar non-active side opposite the active side. The active electrode(s) are disposed on the active side, and are insulated from the non-active side to reduce undesirable current flow into tissue and surrounding electrically conducting fluids. In an exemplary embodiment, the non-active side of tongue-shaped end portion includes a substantially planar support member underlying and insulated from the active electrode(s). The support member provides support for the cantilevered electrode(s), and it has a substantially smooth, atraumatic surface opposite the active electrode(s) to minimize damage to tissue.

The active electrode(s) will usually be formed with edges, corners, surface asperities or the like to maximize the electric field intensities around the electrode surfaces. In a preferred configuration, the probe includes a plurality of active electrodes extending axially from the distal end of the shaft and having a semi-cylindrical cross-section formed by, for example, removing material from a-round or hollow tube. The electrodes are spaced from each other and supported by the underlying tongue-shaped support member. The edges formed by the semi-cylindrical cross-section will face away from the support member to form an active, high electric field intensity zone for ablation of tissue. In an exemplary embodiment, the electrodes are electrically isolated from each other and coupled to current-limiting elements or circuitry to limit current flow based on the impedance between the active electrode and the return or dispersive electrode.

Similar to previous embodiments, the planar ablation probe will usually include a return electrode to facilitate operation in the bipolar mode. However, the probe can be utilized in the monopolar mode with a separate, dispersive electrode pad attached to the patient's skin, for example. In one configuration, the shaft of the probe comprises an electrically conducting material with an insulating layer covering the conducting material to protect surrounding tissue from electric current. The shaft includes an exposed portion spaced proximally from the active electrode(s) to generate a current return path therebetween.

A further understanding of the nature and advantages of the invention will become apparent by reference to the remaining portions of the specification and drawings.

BRIEF DESCRIPTION OF THE DRAWINGS

FIG. 3 illustrates an introducing sheath of the resectoscope of FIG. 2;

FIG. 4 illustrates the return electrode oversheath of FIG. 2;

FIG. 5 illustrates a cross-sectional view of the proximal portion of the resectoscope of FIG. 2, illustrating the electrical connection with the return electrode oversheath;

FIG. 6 is a cross-sectional view of a proximal portion of the resectoscope in FIG. 2, illustrating the electrical connection with the resecting loop assembly;

FIG. 7 is a top section view of a proximal portion of the resectoscope;

FIG. 8A illustrates the resecting loop assembly of FIG. 2;

FIGS. 16A–16E, 17A, 17B, 18A, 18B, 19, 20A and 20B illustrate alternative electrode configurations according to the present invention;

DESCRIPTION OF THE PREFERRED EMBODIMENT

Figure 1:
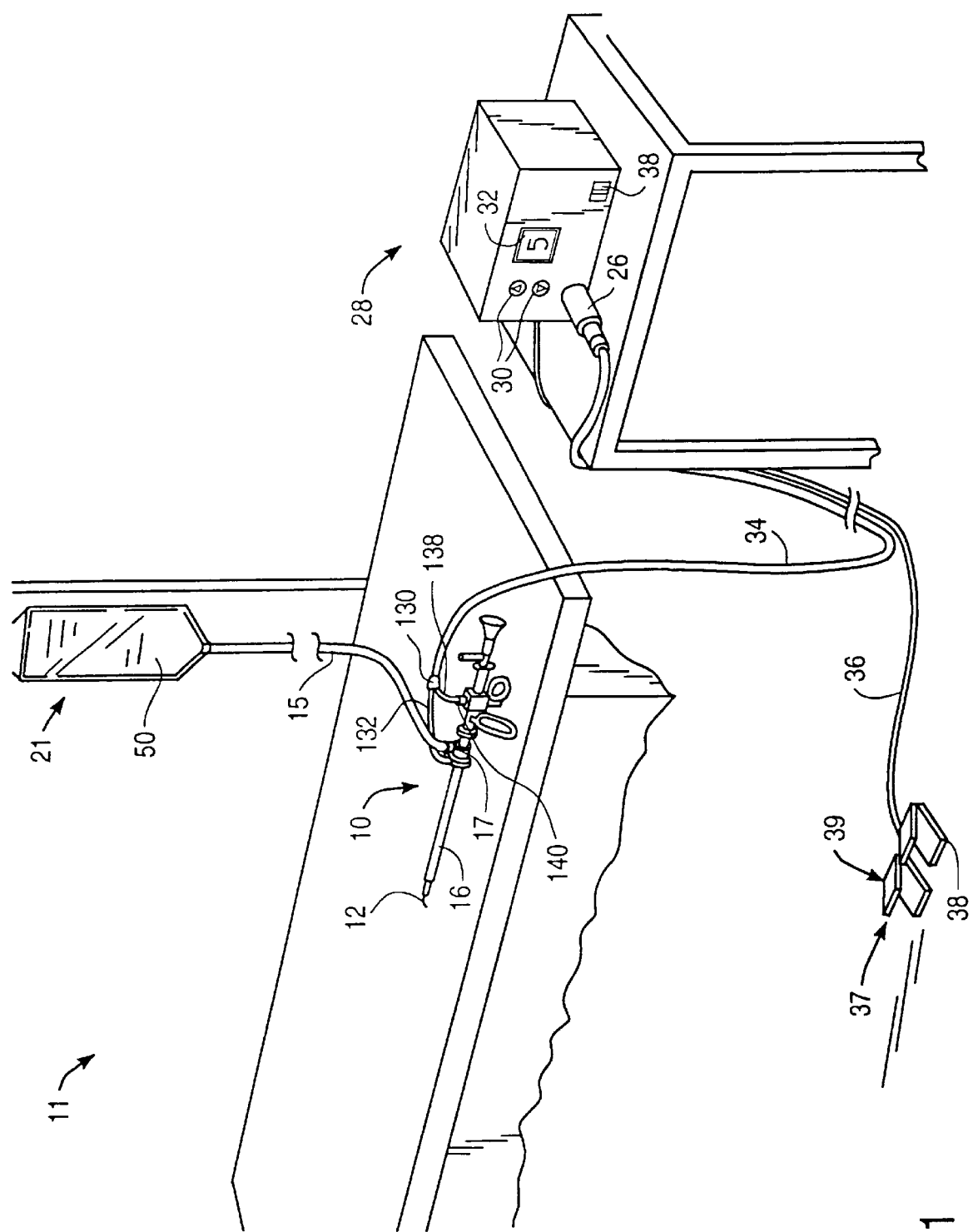
FIG. 1 is a perspective view of a representative electrosurgical system including an electrosurgical resectoscope, an electrically conducting liquid supply and an electrosurgical power supply constructed in accordance with the principles of the present invention.

The present invention provides a system and method for selectively applying electrical energy to a target location within or on a patient's body, such as solid tissue or the like, particularly including procedures within confined spaces such as the spaces around the articular cartilage between the femur and tibia and spaces between adjacent vertebrae in the patient's spine, and procedures that involve resection of relatively larger pieces of tissue. For convenience, the remaining disclosure will be directed specifically to the resection of prostate tissue, and the cutting, shaping or ablation of meniscal tissue located adjacent articular cartilage and soft tissue covering vertebrae. However, it will be appreciated that the system and method can be applied equally well to procedures involving other tissues of the body, as well as to other procedures including open surgery, laparoscopic surgery, thoracoscopic surgery, and other endoscopic surgical procedures. Examples of such procedures include oral procedures, including gingival tissues and mucosal tissues located in the mouth or epidermal tissue on the outer skin, dermatological procedures, such as the treatment of tumors, abnormal tissues, and the like or, canalizing or boring channels or holes through tissue, such as the ventricular wall during transmyocardial revascularization procedures. Other procedures include laminectomy/ disketomy procedures for treating herniated disks, decompressive laminectomy for stenosis in the lumbosacral and cervical spine, posterior lumbosacral and cervical spine fusions, treatment of scoliosis associated with vertebral disease, foraminotomies to remove the roof of the intervertebral foramina to relieve nerve root compression and anterior cervical and lumbar diskectomies. The present invention is also useful for resecting tissue within accessible sites of the body that are suitable for electrode loop resection, such as the resection of prostate tissue, leiomyomas (fibroids) located within the uterus and other diseased tissue within the body.

In addition, the present invention is particularly useful in procedures where the tissue site is flooded or submerged with an electrically conducting fluid, such as isotonic saline. Such procedures, e.g., arthroscopic surgery and the like, are described in detail in co-pending PCT International Application, U.S. National Phase Ser. No. PCT/US94/ 05168, filed on May 10, 1994, the complete disclosure of which has been incorporated herein by reference.

The electrosurgical probe will comprise a shaft having a proximal end and a distal end which supports one or more active electrode(s). The shaft may assume a wide variety of configurations, with the primary purpose being to mechanically support the active electrode(s) and permit the treating physician to manipulate the electrode(s) from a proximal end of the shaft. Usually, the shaft will be a narrow-diameter rod or tube, more usually having dimensions which permit it to be introduced into a body cavity, such as the arthroscopic cavity, through an associated trocar or cannula in a minimally invasive procedure, such as arthroscopic, laparoscopic, thoracoscopic, and other endoscopic procedures. Thus, the shaft will typically have a length of at least 5 cm for oral procedures and at least 10 cm, more typically being 20 cm, or longer for endoscopic procedures. The shaft will typically have a diameter of at least 1 mm and frequently in the range from 1 to 10 mm. In the case of open surgical procedures or procedures on the external portions of the patient's body (e.g., the skin), the shaft may have any suitable length and diameter that would facilitate handling by the surgeon.

The shaft may be rigid or flexible, with flexible shafts optionally being combined with a generally rigid external tube for mechanical support. Flexible shafts may be combined with pull wires, shape memory actuators, and other known mechanisms for effecting selective deflection of the distal end of the shaft to facilitate positioning of the electrode(s) The shaft will usually include a plurality of wires or other conductive elements running axially therethrough to permit connection of the electrode(s) to a connector at the proximal end of the shaft. Specific shaft designs will be described in detail in connection with the figures hereinafter.

The present invention may use a single active electrode or an electrode array distributed over a distal contact surface of a probe. In the case of an electrode array, the array usually includes (but is not limited to) a plurality of independently current-limited and/or power-controlled electrodes to apply electrical energy selectively to the target tissue while limiting the unwanted application of electrical energy to the surrounding tissue and environment resulting from power dissipation into surrounding electrically conductive liquids, such as blood, normal saline, and the like. The electrodes may be independently current-limited by isolating the electrodes from each other and connecting each electrodes to a separate power source that is isolated from the other electrode terminals. Alternatively, the electrodes may be connected to each other at either the proximal or distal ends of the probe to form a single wire that couples to a power source.

In an exemplary embodiment, each individual electrode in the electrode array is electrically insulated from all other electrodes in the array within said probe and is connected to a power source which is isolated from each of the other electrodes in the array or to circuitry which limits or interrupts current flow to the electrode when low resistivity material (e.g., blood or electrically conductive saline irrigant) causes a lower impedance path between the common electrode and the individual electrode terminal. The isolated power sources for each individual electrode may be separate power supply circuits having internal impedance characteristics which limit power to the associated electrode terminal when a low impedance return path is encountered, may be a single power source which is connected to each of the electrodes through independently actuatable switches or may be provided by independent current limiting elements, such as inductors, capacitors, resistors and/or combinations thereof. The current limiting elements may be provided in the probe, connectors, cable, controller or along the conductive path from the controller to the distal tip. Alternatively, the resistance and/or capacitance may occur on the surface of the active electrode(s) due to oxide layers which form selected electrode terminals (e.g., titanium or a resistive coating on the surface of metal). A more complete description of a system and method for selectively limiting current to an array of isolated electrode terminals can be found in commonly assigned, co-pending application Ser. No. 08/561,958, filed Nov. 22, 1996 (attorney docket No. 16238-000700), the complete disclosure of which has already been incorporated herein by reference.

It should be clearly understood that the invention is not limited to electrically isolated electrode terminals, or even to a plurality of electrode terminals. For example, the array of active electrode terminals may be connected to a single lead that extends through the probe shaft to a power source of high frequency current. Alternatively, the probe may incorporate a single electrode that extends directly through the probe shaft or is connected to a single lead that extends to the power source.

In the case of a single electrode, the invention may also use current limiting means to apply electrical energy selectively to the target tissue while limiting the unwanted application of electrical energy to the surrounding tissue. In this embodiment, the electrode may be connected to current limiting elements or to circuitry which limits or interrupts current flow to the electrode when low resistivity material (e.g., blood or electrically conductive saline irrigant) causes a lower impedance path between the common electrode and the electrode. The current limiting elements or circuitry may be configured to completely interrupt or modulate current flow to the electrode, for example, when a certain percentage of the electrode surface is in contact with low resistivity material. In one embodiment, the current flow will be modulated or completely interrupted when, for example, a large portion of the electrode surface is exposed to fluids and, therefore, not in contact with the target tissue. In this manner, current can be selectively applied to the target tissue, while minimizing current flow to surrounding fluids and adjacent non-target tissue structures.

According to the present invention, the active electrode(s) will have an active portion or surface with surface geometries shaped to promote the electric field intensity and associated current density along the leading edges of the electrodes. Suitable surface geometries may be obtained by creating electrode shapes that include preferential sharp edges, or by creating asperities or other surface roughness on the active surface(s) of the electrodes. Electrode shapes according to the present invention can include the use of formed wire (e.g., by drawing round wire through a shaping die) to form electrodes with a variety of cross-sectional shapes, such as square, rectangular, L or V shaped, or the like. Electrode edges may also be created by removing a portion of the elongate metal electrode to reshape the cross-section. For example, material can be ground along the length of a round or hollow wire electrode to form D or C shaped wires, respectively, with edges facing in the cutting direction. Alternatively, material can be removed at closely spaced intervals along the electrode length to form transverse grooves, slots, threads or the like along the electrodes.

Additionally or alternatively, the active electrode surface (s) may be modified through chemical, electrochemical or abrasive methods to create a multiplicity of surface asperities on the electrode surface. These surface asperities will promote high electric field intensities between the active electrode surface(s) and the target tissue to facilitate ablation or cutting of the tissue. For example, surface asperities may be created by etching the active electrodes with etchants having a PH less than 7.0 or by using a high velocity stream of abrasive particles (e.g., grit blasting) to create asperities on the surface of an elongated electrode.

Additionally or alternatively, the active electrode surface (s) may be provided by assembling alternating layers of electrically conductive members (i.e., electrodes) and electrically insulating spacers. By way of example, an active electrode having multiple circular edges may be constructed using alternating layers of concentric, thin metal washers (e.g., titanium, stainless steel or the like), having outside diameters D. The washers may be separated by thin concentric insulating spacers (e.g., anodized aluminum, ceramic, glass, glass ceramic, plastic, etc.) having an outside diameter D' which is less than D so that the edges of the metal washers extend beyond the insulating spacers. The electrode assembly can be constructed by placing the metal washers over a central, electrically conductive mandrel, which provides for electrical communication between the power source and the multiple metal "washer" shaped electrodes. In this arrangement, the electrodes are preferably at the same source polarity since they are in contact with a common electrical lead (i.e., mandrel).

Alternatively, the electrode assembly may include a split mandrel having opposite polarities such that adjacent metal washers are at opposite polarities to effect one or more pairs of bipolar washer shaped electrodes. In this configuration, the metal electrodes may have any shape suitable for the intended ablation or resection of tissue, e.g., square, circular, hexagonal octagonal, triangular, etc. In addition, the perimeter of the thin metal electrode may be stamped, machined, notched or otherwise modified to increase the electric field intensity at the working (outer) surface of the metal electrode. Also, the metal electrodes (e.g., metal washers) may be coated with an electrically insulating layer (e.g., ceramic, glass or porcelain) of sufficient thickness to provide spacing between adjacent electrode members, whether the electrode assembly is monopolar or bipolar. The insulating coating may extend up to the perimeter of the metal electrode (e.g., washer), or it may be recessed from the perimeter to expose a greater portion of the edges of the electrodes.

In another aspect of the invention, the active electrodes will also have a "non-active" portion or surface(s) to selectively reduce undesirable current flow from the non-active portion or surface(s) into tissue or surrounding electrically conducting liquids (e.g., isotonic saline, blood or blood/non-conducting irrigant mixtures). Preferably, the "non-active" electrode surface(s) will be coated with an electrically insulating material. This can be accomplished, for example, with plasma deposited coatings of an insulating material, thin-film deposition of an insulating material using evaporative or sputtering techniques (e.g., $SiO_2$ or $Si_3N_4$), dip coating or by providing an electrically insulating support member to electrically insulate a portion of the external surface of the electrode.

The method of the present invention comprises positioning an electrosurgical probe adjacent the target tissue so that at least one active electrode is brought into close proximity to the target site. A return electrode is positioned within an electrically conducting liquid, such as isotonic saline, to generate a current flow path between the target site and the return electrode. High frequency voltage is then applied between the active and return electrode through the current flow path created by the electrically conducting licuid in either a bipolar or monopolar manner. The probe may then be translated, reciprocated or otherwise manipulated to cut the tissue or effect the desired depth of ablation.

The current flow path may be generated by submerging the tissue site in an electrical conducting fluid (e.g., arthroscopic surgery and the like) or by directing an electrically conducting liquid along a fluid path past the return electrode and to the target site to generate the current flow path between the target site and the return electrode. This latter method is particularly effective in a dry environment (i.e., the tissue is not submerged in fluid), such as open, endoscopic or oral surgery, because the electrically conducting liquid provides a suitable current flow path from the target site to the return electrode. A more complete description of an exemplary method of directing electrically conducting fluid between the active and return electrodes is described in Ser. No. 08/485,219, filed Jun. 7, 1995 (docket no. 16238-000600), previously incorporated herein by reference. The active electrode(s) are preferably disposed at the distal end of the probe and the return electrode is spaced from the active electrode and enclosed within an insulating sheath. This minimizes exposure of the return electrode to surrounding tissue and minimizes possible shorting of the current between the active and return electrodes. In endoscopic procedures, the probe will typically be passed through a conventional trocar cannula while viewing of the operative site is provided through the use of an endoscope disposed in a separate cannula.

In the method of the present invention, a high frequency voltage is applied between the active portion of the active electrode(s) and the return electrode to develop high electric field intensities in the vicinity of the target tissue site. The high electric field intensities lead to electric field induced molecular breakdown of target tissue through molecular dissociation (rather than thermal evaporation or carbonization). Applicant believes that the tissue structure is volumetrically removed through molecular disintegration of larger organic molecules into smaller molecules and/or atoms, such as hydrogen, oxides of carbon, hydrocarbons and nitrogen compounds. This molecular disintegration completely removes the tissue structure, as opposed to dehydrating the tissue material by the removal of liquid within the cells of the tissue, as is typically the case with electrosurgical desiccation.

The high electric field intensities may be generated by applying a high frequency voltage that is sufficient to vaporize the electrically conducting liquid over at least a portion of the active electrode(s) in the region between the distal tip of the active electrode and the target tissue. Since the vapor layer or vaporized region has a relatively high electrical impedance, it increases the voltage differential between the active electrode tip and the tissue and causes ionization within the vapor layer due to the presence of an ionizable species (e.g., sodium when isotonic saline is the electrically conducting fluid). This ionization, under optimal conditions, induces the discharge of energetic electrons and photons from the vapor layer and to the surface of the target tissue. This energy may be in the form of energetic photons (e.g., ultraviolet radiation), energetic particles (e.g., electrons) or a combination thereof. A more detailed description of this phenomena can be found in Ser. No. 08/561,958, the complete disclosure of which has already been incorporated herein by reference.

The voltage applied between the return electrode and the active electrode(s) will be at high or radio frequency, typically between about 5 kHz and 20 MHz, usually being between about 30 kHz and 2.5 MHz, and preferably being between about 50 kHz and 400 kHz. The RMS (root mean square) voltage applied will usually be in the range from about 5 volts to 1000 volts, preferably being in the range from about 50 volts to 800 volts, and more preferably being in the range from about 100 volts to 400 volts. These frequencies and voltages will result in peak-to-peak voltages and currents that are sufficient to vaporize the electrically conductive liquid and, in turn, create the conditions within the vaporized region which result in high electric fields and emission of energetic photons and/or electrons to ablate tissue. Typically, the peak-to-peak voltage will be in the range of 200 to 2000 volts and preferably in the range of 300 to 1600 volts and more preferably in the range of 500 to 1200 volts.

The preferred power source of the present invention delivers a high frequency voltage selectable to generate average power levels ranging from tens of milliwatts to tens of watts up to hundreds of watts per electrode, depending on the number of electrodes, the target tissue being ablated, the rate of ablation desired or the maximum allowed temperature selected for the probe tip. The power source allows the user to select the voltage level according to the specific requirements of a particular oral surgery, dermatological procedure, open surgery or other endoscopic surgery procedure.

The power source may be current limited or otherwise controlled so that undesired heating of electrically conductive fluids or other low electrical resistance media does not occur. In a presently preferred embodiment of the present invention, current limiting inductors are placed in series with each independent electrode terminal, where the inductance of the inductor is in the range of 10 uH to 50,000 uH, depending on the geometry and size of the electrode(s), the electrical properties of the target tissue, the desired ablation rate and the operating frequency. Alternatively, capacitor-inductor (LC) circuit structures may be employed, as described previously in co-pending PCT application No. PCT/US94/05168, the complete disclosure of which is incorporated herein by reference. Additionally, current limiting resistors may be selected. Preferably, these resistors will have a large positive temperature coefficient of resistance so that, as the current level begins to rise for any individual electrode in contact with a low resistance medium (e.g., saline irrigant), the resistance of the current limiting resistor increases significantly, thereby minimizing the power delivery from said electrode into the low resistance medium (e.g., saline irrigant).

As an alternative to such passive circuit structures, regulated current flow to each electrode terminal may be provided by a multi-channel power supply. A substantially constant current level for each individual electrode terminal within a range which will limit power delivery through a low resistance path, e.g., isotonic saline irrigant, and would be selected by the user to achieve the desired rate of cutting or ablation. Such a multi-channel power supply thus provides a substantially constant current source with selectable current level in series with each electrode terminal, wherein all electrodes will operate at or below the same, user selectable maximum current level. Current flow to all electrode terminals could be periodically sensed and stopped if the temperature measured at the surface of the electrode array exceeds user selected limits. Particular control system designs for implementing this strategy are well within the skill of the art.

Yet another alternative involves the use of a power supply for energizing one or more electrodes having use of one or more channels of user-selectable voltage levels. The channels would incorporate an active control mechanism for limiting current levels below a preselected maximum level. The preselected maximum current level depends on the size and configuration of the electrode(s), and may be "factory" set or user selectable. Alternatively, an indicator device may be included in the probe (e.g., a resistor having a resistance value which corresponds to the maximum current level appropriate to a specific electrode configuration) such that the power supply can (1) first measure the indicator device value (e.g., measure the resistance of the indicator) contained within the probe; and (2) then set the maximum current level which corresponds to that resistance value. In this manner, a range of probe designs having greatly differing electrode size(s) and configuration(s) can be energized since the power supply will automatically adjust the maximum current level to correspond to each particular electrode size and configuration.

Yet another alternative involves the use of one or several power supplies which allow one or several electrodes to be simultaneously energized and which include active control means for limiting current levels below a preselected maximum level. In this arrangement, only one or several electrodes would be simultaneously energized for a brief period. Switching means would allow the next one or several electrodes to be energized for a brief period. By sequentially energizing one or several electrodes, the interaction between adjacent electrodes can be minimized (for the case of energizing several electrode positioned at the maximum possible spacing within the overall envelope of the electrode array) or eliminated (for the case of energizing only a single electrode at any one time). As before, a resistance measurement means may be employed for each electrode prior to the application of power wherein a (measured) low resistance (below some preselected level) will prevent that electrode from being energized during a given cycle. By way of example, the sequential powering and control scheme of the present invention would function in a manner similar to an automobile distributor. In this example, an electrical contact rotates past terminals connected to each spark plug. In this example, each spark plug corresponds to the exposed surface of each of the electrodes. In addition, the present invention includes the means to measure the resistance of the medium in contact with each electrode and cause voltage to be applied only if the resistance exceeds a preselected level.

During the surgical procedure, the distal end of the probe or the active electrode(s) will usually be maintained at a small distance away from the target tissue surface. This small spacing allows for the continual resupply of electrically conducting liquid into the interface between the active electrode(s) and the target tissue surface. This continual resupply of the electrically conducting liquid helps to ensure that the thin vapor layer will remain between active electrode(s) and the tissue surface. In addition, dynamic movement of the active electrode(s) over the tissue site allows the electrically conducting liquid to cool the tissue surrounding recently ablated areas to minimize thermal damage to this surrounding tissue. Typically, the active electrode(s) will be about 0.02 to 2 mm from the target tissue and preferably about 0.05 to 0.5 mm during the ablation process. One method of maintaining this space is to translate and/or rotate the probe transversely relative to the tissue, i.e., a light brushing motion, to maintain a thin vaporized layer or region between the active electrode and the tissue. Of course, if coagulation of a deeper region of tissue is necessary (e.g., for sealing a bleeding vessel imbedded within the tissue), it may be desirable to press the active electrode(s) against the tissue to effect joulean heating therein.

In one embodiment of the invention, the active electrode or the electrode array will have an exposed length in the range from about 2.5 to 12.5 mm. With these electrode lengths, applicant has found that current-limiting inductors having values of about 0 to 100 uH, preferably about 25 to 50 uH, are suitable for establishing the requisite conditions for selective ablation described above (i.e., the generation of sufficient electric field intensities to form a vapor layer in the electrically conducting liquid and to induce the discharge of energy through the vapor layer to ablate tissue while minimizing substantial necrosis beyond several cell layers). Of course, the active electrode(s) may have a substantially smaller exposed length away from the probe than described above (on the order of about 0 to 0.5 mm). This configuration is described in Ser. No. 08/561,958 (attorney docket 16238-000700), the complete disclosure of which has already been incorporated herein by reference.

Referring to the drawings in detail, wherein like numerals indicate like elements, an electrosurgical system 11 is shown constructed according to the principles of the present invention. Referring to FIG. 1, electrosurgical system 11 generally comprises an electrosurgical resectoscope 10 incorporating a resecting loop assembly 12 with an active electrode (not shown in FIG. 1), and a return electrode oversheath 16 circumscribing a portion of the resecting loop assembly 12. The resectoscope 10 is connected to a power supply 28 for providing high frequency voltage to the active electrode and a liquid source 21 for supplying electrically conducting fluid 50 to a target tissue (see FIGS. 21 and 22). A liquid supply tube 15 removably couples liquid source 21, (e.g., a bag of fluid elevated above the surgical site or having a pumping device), with return electrode oversheath 16. A manual control valve 17 may also be provided between the proximal end of return electrode 16 and supply tube 15 to allow the surgical team to regulate the flow of electrically conducting liquid 50.

Power supply 28 has a selector 30 for varying the applied voltage level. Power supply 28 also includes a mechanism for energizing the active electrode of resectoscope 10 through the depression of a pedal 39 in a foot pedal 37 positioned close to the user. The foot pedal 37 will usually include a second pedal 38 for remotely adjusting the energy level applied to electrode 14. In an exemplary configuration, first pedal 37 will apply a higher voltage level suitable for cutting and ablating tissue and second pedal 38 will apply a lower voltage level suitable for coagulating and sealing tissue, such as a transected blood vessel (discussed in further detail below). A specific design of one power supply which may be used with the electrosurgical probe of the present invention is described in parent application PCT US 94/051168, the full disclosure of which has previously been incorporated herein by reference.

Figure 2:
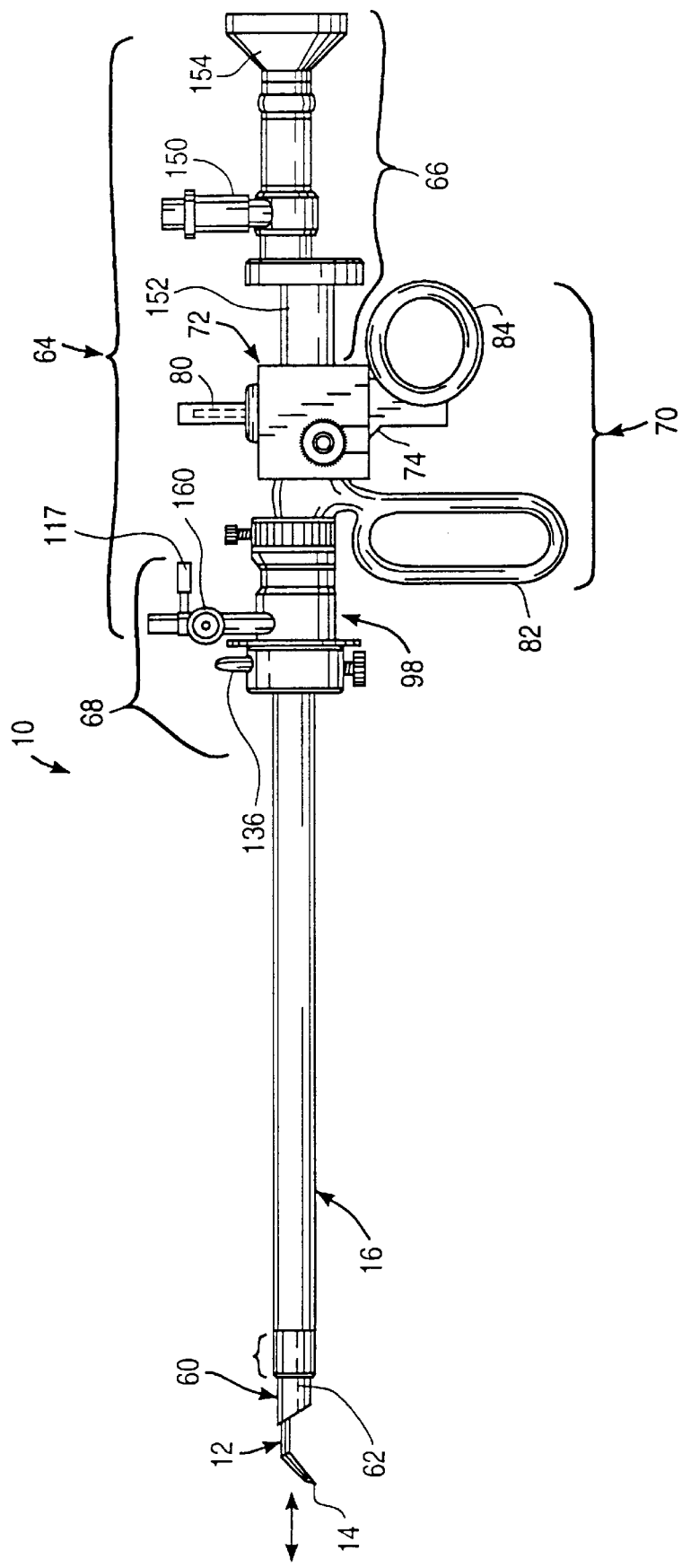
FIG. 2 is an enlarged perspective view of the resectoscope of FIG. 1 incorporating a return electrode oversheath and a resecting loop assembly according to the present invention.
Figure 8B:
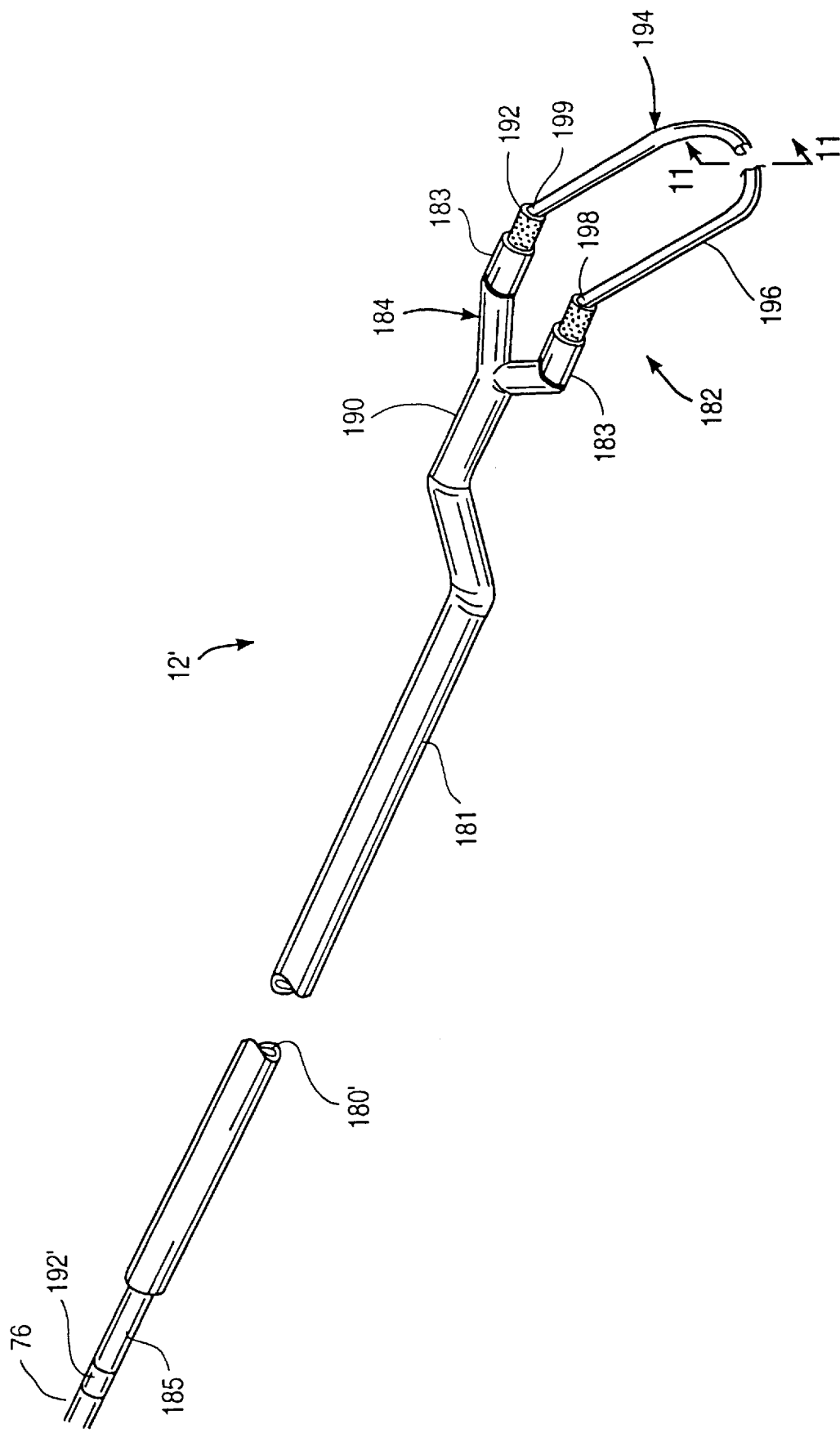
FIG. 8B illustrates an alternative resecting loop assembly incorporating a return electrode.

Referring to FIGS. 2–11, resectoscope 10 is preferably a conventional or specialized resectoscope that is adapted for use with resecting loop assembly 12 and return electrode oversheath 16 according to the present invention. Existing resectoscopes useful with the present invention can be found under the trade names of USA Elite System Resectoscope from Circon/ACMI of Stamford, Conn. and OES Resectoscope from Olympus Corporation of Lake Success, N.Y. Loop assembly 12 and oversheath 16 may also be used without a resectoscope. In this configuration, the surgeon may use other means for viewing the surgical site, such as other endoscopes. Resectoscope 10 generally includes a proximal handle 64, and an introducing sheath 60 (FIG. 3) having a hollow, tubular shaft 62 for axially receiving loop assembly 12. Sheath 60 also includes a proximal hub 98 for connecting sheath 60 to handle 64 and return electrode oversheath 16 (discussed in detail below). As shown in FIG. 2, handle 64 includes a viewing assembly 66, an irrigant/suction assembly 68 and an actuation assembly 70 for axially reciprocating loop assembly 12 relative to shaft 62.

Referring to FIGS. 2, 6 and 7, actuation assembly 70 includes a coupling housing 72 having an outer knob or thumbscrew 74 that can be tightened to secure a proximal connector leg 76 of loop assembly 12 to an electrically conducting inner sleeve member 78 of coupling housing 72 (FIG. 7). Sleeve member 78 electrically couples leg 76 to a resecting loop terminal 80 (FIG. 6), which can be removably coupled to power supply 28 to provide power to loop assembly 12 (discussed in further detail below). Coupling housing 72 is axially translatable relative to introducing sheath 60 so that resecting loop assembly 12 can be axially translated relative to the distal end 94 of tubular shaft 62 (see FIG. 3). As shown in FIG. 2, resectoscope 10 will usually include a finger loop 82 and a thumb loop 84 suitably connected to housing 72 for reciprocating housing 72 and loop assembly 12 relative to the distal end 94 of shaft 62. Of course, it will be recognized that other control means for axially reciprocating loop assembly 12 can be utilized with the present invention, such as rotatable knobs, trigger buttons, and the like.

Referring to FIGS. 4 and 5, electrosurgical system 11 will preferably include a return electrode oversheath 16 for completing the current path between active electrode 14 and power supply 28 (discussed in detail below). It should be made clear, however, that the present invention is not limited to a bipolar modality and, may utilize a monopolar mode. In this configuration, return electrode oversheath 16 is not required. Instead, voltage is applied between an active electrode 14 and a dispersive electrode plate externally attached to the patient's skin such that electric current flows from active electrode 14, through the patient's body, to the dispersive electrode.

Return electrode oversheath 16 generally includes an electrically conducting, hollow shaft 86 coupled to a proximal housing 88 with a suitable epoxy adhesive, for example. The inner and outer surfaces of shaft 86 are covered with an electrically insulating layer 90 over the entire length of shaft 86 except for a distal end portion 92, which remains exposed to generate a current path from active loop assembly 12 (discussed below). Electrically insulating layer 90 may comprise a heat shrinkable tubing material, such as Kynar™, or it may be a deposited coating, such as Parylene™, polytetrafluoroethylene, polyimide, or the like. The provision of the electrically insulating layer 90 over return electrode shaft 86 prevents direct electrical contact between the return electrode and any adjacent body structure or the surgeon. Such direct electrical contact between a body structure (e.g., tendon) and an exposed return electrode member could result in unwanted heating and necrosis of the structure at the point of contact causing necrosis. If return electrode oversheath 16 is being used with an electrically insulating resectoscope sheath (e.g., a plastic tubular sheath), the inner surface of shaft 86 may remain exposed (i.e., no electrically insulating layer 90).

Return electrode shaft 86 will have an inner diameter large enough to slide shaft 86 over tubular shaft 62 of introducing sheath 60 (FIG. 5). Distal end portion 94 of shaft 62 is introduced through an opening 96 in proximal housing 88 and axially delivered through return electrode shaft 86 until housing 88 abuts against proximal hub 98 of introducing sheath 60. Return electrode oversheath 16 further includes a fastener, such as a thumbscrew 100, to secure the return electrode to introducing sheath 60. As shown in FIG. 5, return electrode shaft 86 has an opening 102 aligned with thumbscrew 100 so that the thumbscrew 100 can engage tubular shaft 62 of introducing sheath 60. Thumbscrew 100 preferably comprises an electrically insulating material, such as Ultem™, to minimize electrical shock to the surgeon during use of resectoscope 10.

Figure 21:
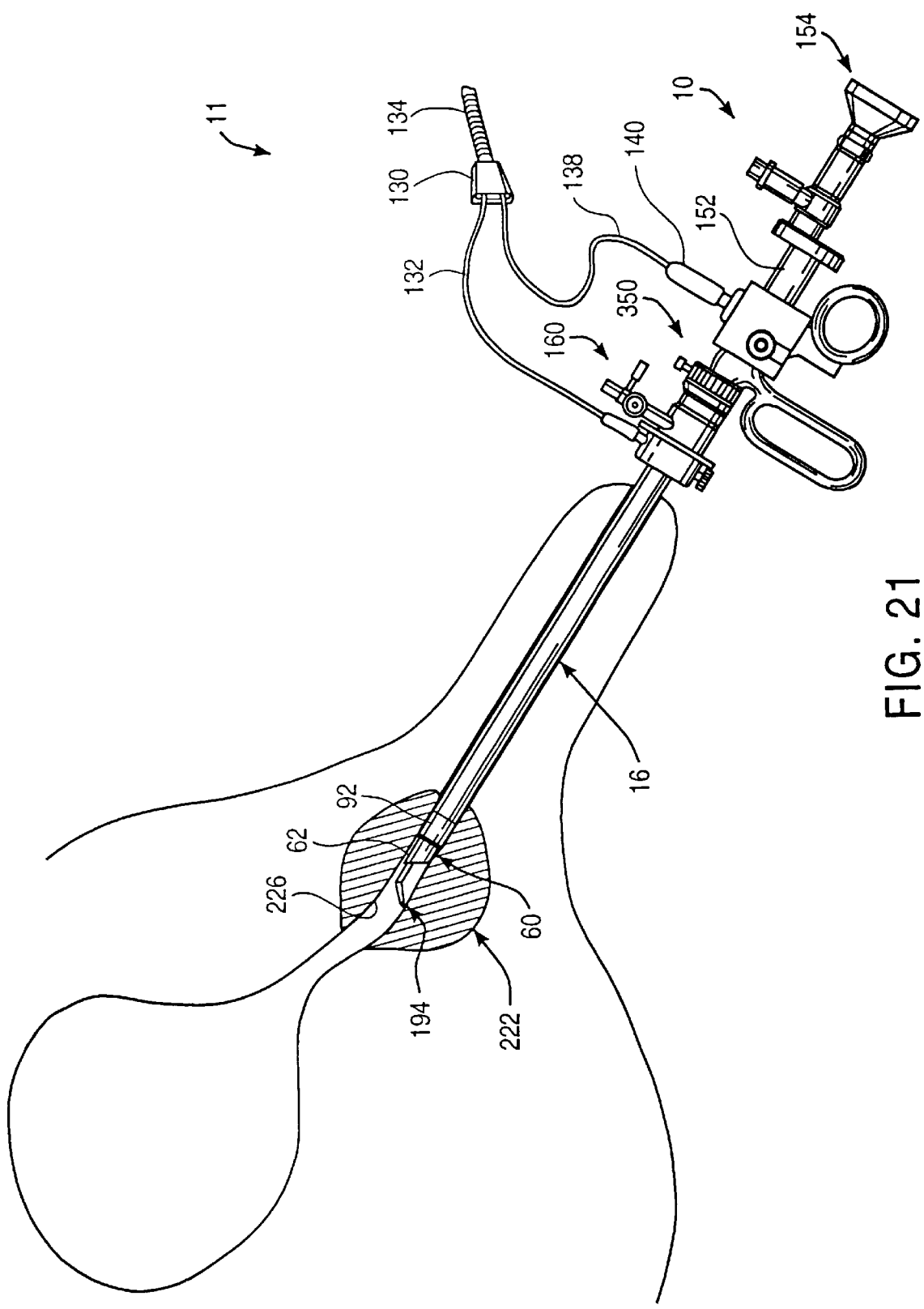
FIG. 21 illustrates a method of transurethral resection of prostate tissue with the electrosurgical system of FIG. 1.

Referring to FIGS. 1 and 5, resectoscope 10 is electrically connected to power supply 28 with cable 34, which is removably connected to power supply 28 by a power supply connector plug 26. Cable 34 includes an adaptor 130 that branches into a first lead 132 which is removably connected via plug 134 to a return electrode terminal 136, e.g., a minibananna plug, and a second lead 138 which is removably connected via plug 140 to resecting loop terminal 80 (FIG. 21). As shown in FIG. 5, return electrode plug 134 includes a recessed electrical receptacle 142 which permits plug 134 to be inserted into a cavity 144 of return electrode housing 88. This provides a fluid-tight seal between housing 88 and plug 134 to minimize the possibility of electrical shock to the surgeon or patient if the controller is energized prior to the complete connection of plug 134 and electrode terminal 136.

As mentioned above, handle 64 of resectoscope 10 will also usually include a viewing assembly 66 and an irrigant/suction assembly 68. As shown in FIG. 2, viewing assembly 66 includes a hub 150, a telescopic lumen 152 extending through shaft 62 of introducing sheath 60 and an eyepiece 154 coupled to lumen 152 to permit viewing of the target site by the physician. Alternatively, a camera (not shown) may be attached to the proximal end of hub 150 to allow display of the surgical site on a video monitor. A fiberoptic light source (not shown) is typically attached to hub 150 to illuminate the target site. Irrigant/suction assembly 68 includes proximal hub 98 of introducing sheath 60, and a connector 160 extending from hub 98 and coupled to supply line 15 for introducing a sterile irrigant, typically isotonic saline, to the surgical site. Connector 160 is fluidly coupled to an axial lumen 162 within shaft 62 (see FIG. 3). Fluid may also be withdrawn through axial lumen 162 or a second lumen (also not shown) within shaft 62 to withdraw contaminated fluids from the surgical site and to facilitate the surgeon's view.

Referring to FIGS. 8–11, an exemplary resecting loop assembly 12 according to the present invention will now be described. Loop assembly 12 generally includes an electrically insulating hollow shaft 180 with proximal connection leg 76 and a distal active electrode assembly 182. Active electrode assembly 182 includes a bifurcated support member 184 having a pair of hollow arms 186, 188 extending from a distal end 190 of shaft 180. A hollow, electrically insulating tubular member 192 extends from each arm 186, 188 of bifurcated support member 184, and a tubular resecting loop electrode 194 extends from each tubular member 192. Tubular members 192 will comprise a suitable insulating material (e.g., ceramic or glass material, such as alumina, zirconia and the like). The preferred support matrix material is alumina, available from Kyocera Industrial Ceramics Corporation, Elkgrove, Ill., because of its good electrically insulating properties, high flexural modulus, resistance to carbon tracking, biocompatibility, and high melting point.

Alternatively, resecting loop assembly 12 may incorporate the return electrode so that only a single instrument is required for bipolar resection of tissue (i.e., a return electrode oversheath is not required). By way of example (see FIG. 8B), a resecting loop assembly 12' according to the present invention includes an electrically conducting shaft 180' covered with an outer electrically insulating layer 181. Shaft 180' includes a distal exposed portion 183 for completing the current return path with active electrode assembly 182, and a proximal exposed portion 185 for connecting return electrode 180 to power supply 28. An electrically insulating layer 192 insulates shaft 180 from active electrode 196 and exposed portion 185 from proximal connection leg 76.

Figure 9:
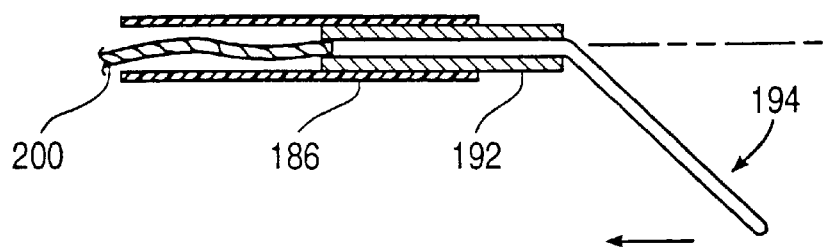
FIG. 9 is a section of a distal portion of the resecting loop assembly of FIG. 5, illustrating a resecting loop electrode.
Figure 10A:
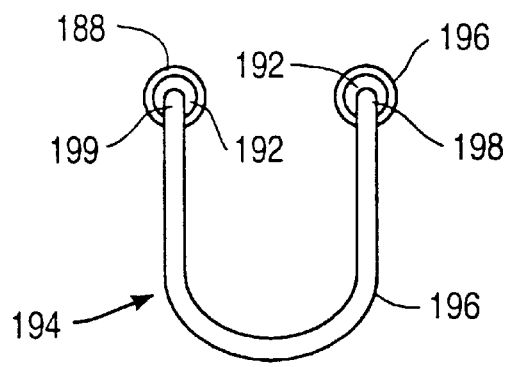
FIG. 10A is a front view of the resecting loop electrode.

As shown in FIGS. 8 and 10A, loop electrode 194 comprises an elongate loop body 196 having first and second ends 198, 199 coupled to and extending within tubular members 192. Resecting loop electrode 194 is preferably composed of a corrosion resistant, electrically conductive metal or alloy, such as platinum, titanium, tantalum, tungsten, stainless steel, nickel and cobalt-based alloys and the like. It should be understood that loop electrode 194 may have configurations other than that described above and shown in FIGS. 8–11. Preferred requirements for electrode 194 are that: (1) the electrode fits within the available space within the working end of a resectoscope, which generally includes fiber optic or "glass rod" optical viewing and lighting means, articulating resecting means and irrigant supply ports; (2) the electrode is shaped and sized to allow the surgeon to view the tissue site; and (3) the electrode is configured to cut chips or small portions of tissue from the target site. Thus, the "loop" electrode may have a variety of shapes, such as semi-circular, square, triangular, rectangular, or multi-sided geometry (see FIGS. 10B–10D, for example). However, the semi-circular loop electrode of FIG. 10A is preferred because it easily fits within the cylindrical bore of conventional resectoscopes. In addition, this shape tends to facilitate good visibility for the surgeon, and it produces rapid resection of tissue.

Loop electrode 194 may also comprise a plurality of active electrodes that are either coupled together or electrically isolated from each other (discussed below). In the latter case, electrosurgical system 11 may include current limiting elements or circuitry to independently limit current to the electrodes based on the impedance between each electrode and return electrode 92, as described above.

Referring to FIGS. 8A and 9, electrical connections 200, such as lead wires, metal tubes or the like, extend through one or both arms 186, 188 of support member 184 and shaft 180 to electrically couple one or both ends 198, 199 of resecting loop electrode 196 with connector leg 76. Electrical connections 200 are coupled to loop electrode 194 and connector leg 74 using crimping, soldering, welding or other suitable methods. Electrical connections 200 are preferably covered with an insulating sheath (not shown) except for exposed distal and proximal portions of connections 200 that are coupled to loop electrode 194 and leg 74, respectively.

Figure 11:
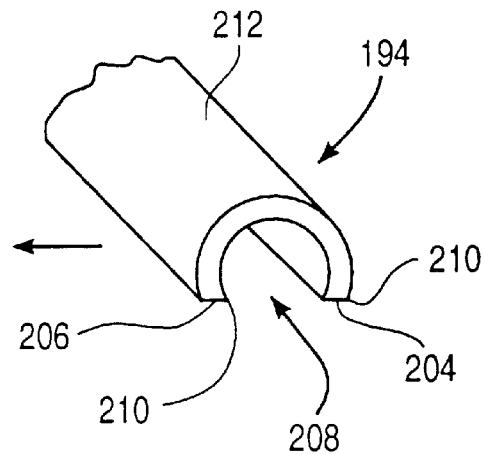
FIG. 11 is an enlarged view of the resecting loop electrode.
Figure 10B:
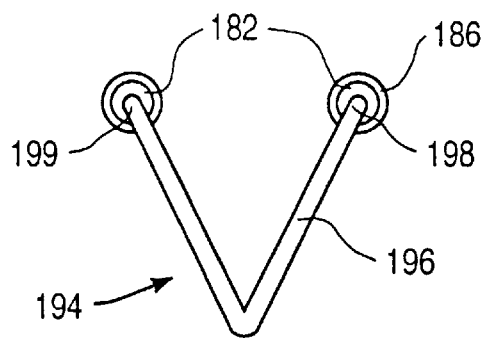
FIGS. 10B–10D illustrate alternative geometries for the resecting loop electrode.
Figure 10C:
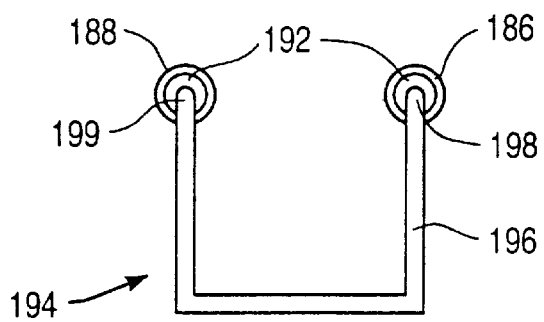
Figure 10D:
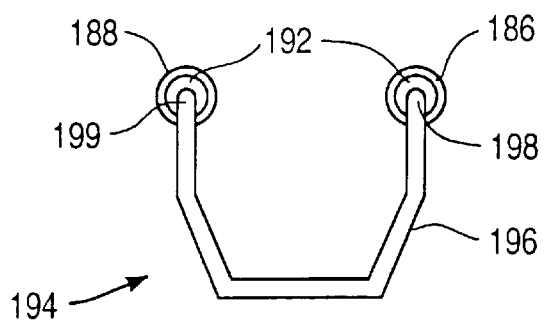
Figure 14:
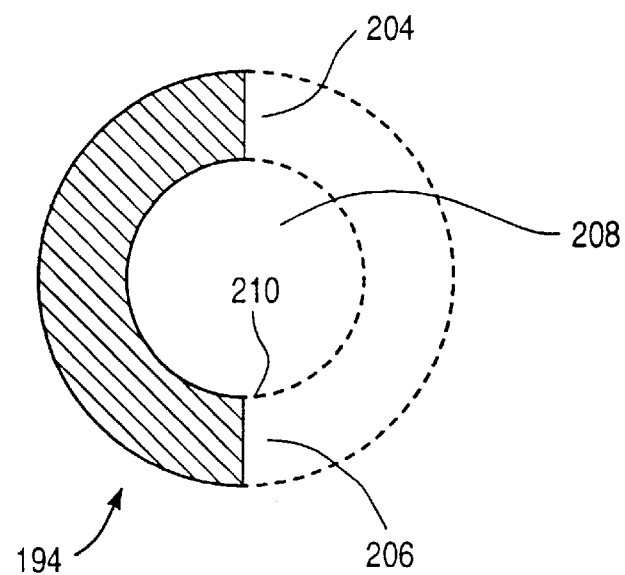
FIG. 14 is a transverse cross-sectional views of the resecting loop electrode of FIG. 9.

As shown in FIG. 11, resecting loop electrode 194 preferably has a semi-cylindrical transverse cross-section along its entire length to form first and second ends 204, 206 that define a slot 208 therebetween. Ends 204, 206 each define relatively sharp edges 210 that promote high electric field intensities around ends 204, 206 to enhance the tissue cutting capabilities of resecting loop assembly 12. Ends 204, 206 and edges 210 of loop electrode 194 form an active portion of electrode that promotes sufficiently high electric field intensities sufficient to reach the threshold conditions for formation of a vapor layer in the electrically conductive liquid, as discussed above. For surgical procedures involving tissue resection, resecting loop electrode 194 is preferably oriented so that ends 204, 206 are generally parallel to the cutting direction (i.e., facing the target tissue, see FIG. 14). This orientation facilitates the formation of a vapor layer between ends 204, 206 and the target tissue and directs the energy induced from the vapor layer to the target tissue.

Figure 12:
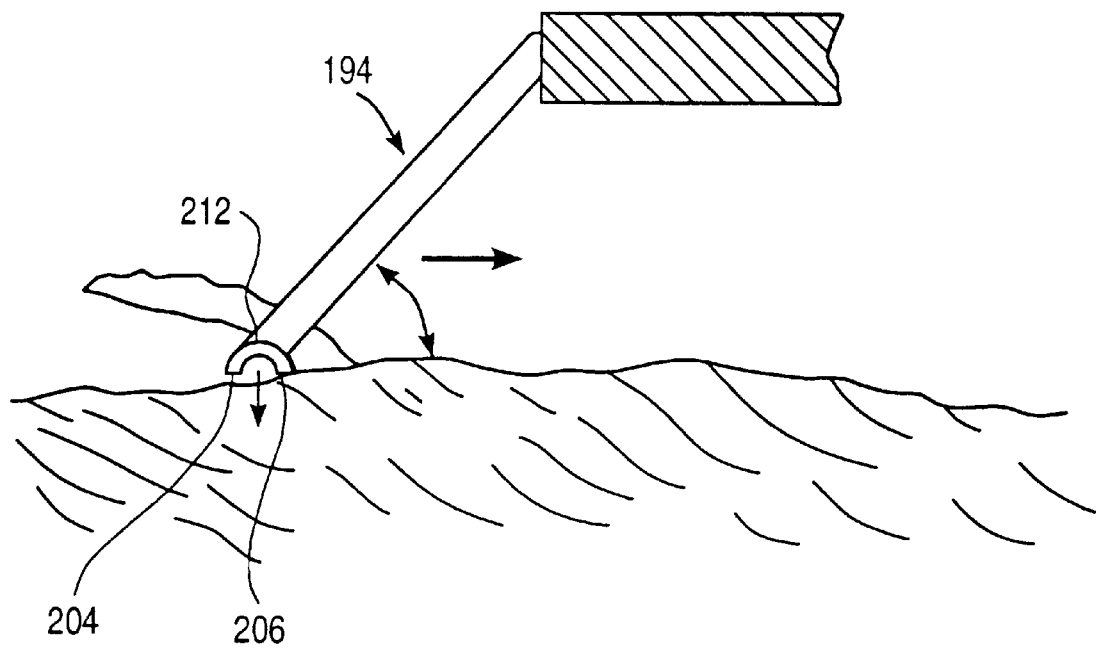
FIG. 12 is a schematic view illustrating the resecting loop electrode of FIG. 9 resecting a tissue portion at a target site.
Figure 13:
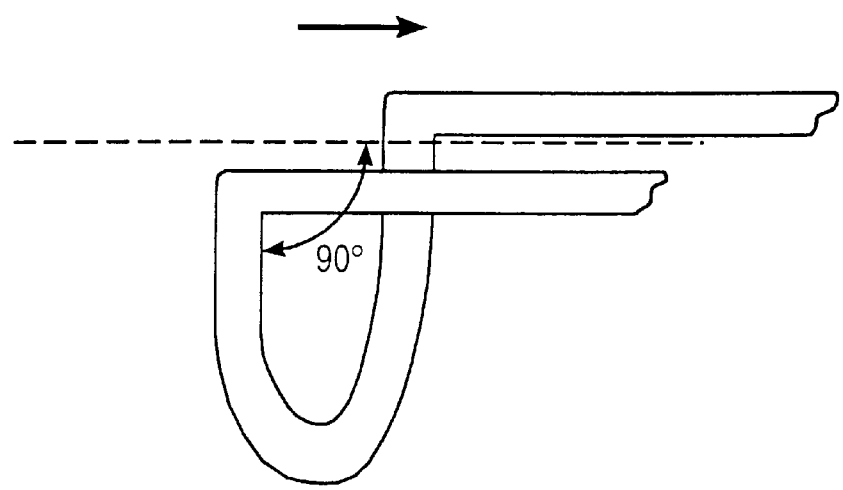
FIG. 13 is an alternative embodiment of the resecting loop electrode of FIG. 9.

As shown in FIGS. 11 and 12, loop electrode 194 further includes a non-active portion 212 on the opposite side from ends 204, 206. Non-active portion 212 preferably defines a relatively smooth surface to reduce the electric field intensities around portion 212, thereby minimizing undesirable current flow into fluids and surrounding tissue. In addition, non-active portion 212 may include an insulating layer (not shown) to further minimize undesirable tissue damage. This configuration allows the surgeon to more selectively ablate tissue at the target site.

In an exemplary configuration, loop electrode 194 is formed from a hollow tube that is filed or ground down to form the semi-circular or "C" shaped cross section. The filing operation creates four relatively sharp corners 210 along the length of the bipolar loop electrode 194, as shown in FIG. 11. In order to maximize the spacing between the inner electrode edges 210 while maintaining the strength of loop electrode 194, the thin metal wall tubing is filed or ground up to, but not exceeding the diametral line of the tubing. Usually, loop electrode 194 will have an outside diameter of about 0.005 to 0.03 inch and a wall thickness of about 0.001 to 0.01 inch.

Figures 15A, 15B:
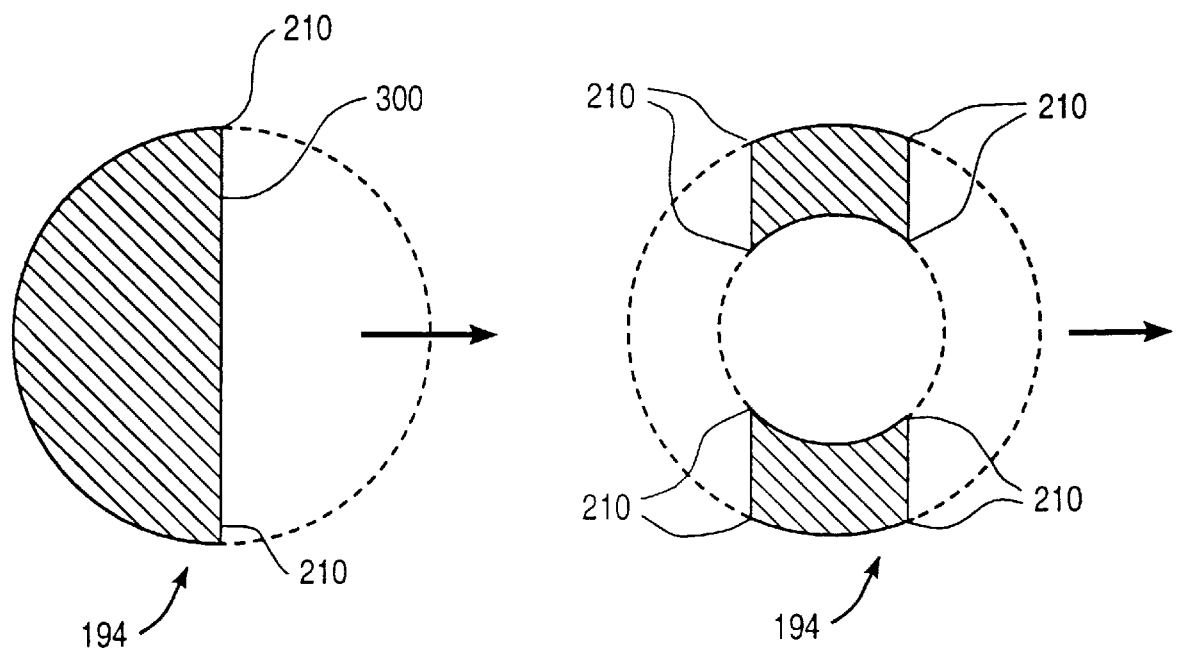
FIGS. 15A and 15B are transverse cross-sectional views of alternative loop electrodes according to the present invention.
Figure 16A:
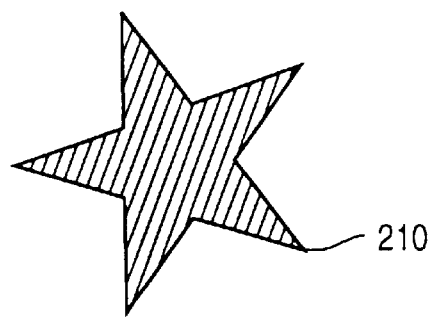
Figure 16B:
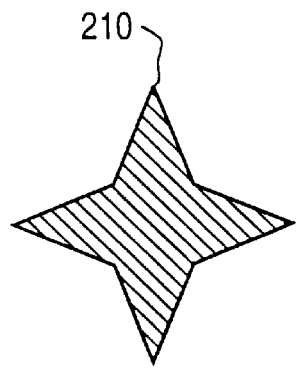
Figure 16C:
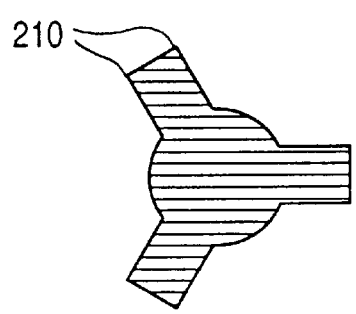
Figure 16D:
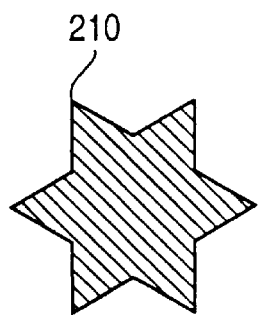
Figure 16E:
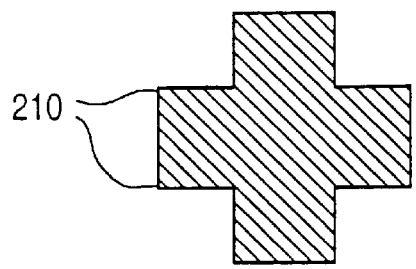

FIGS. 15A and 15B illustrate alternative embodiments of bipolar loop electrode 194. As shown in FIG. 15A, loop electrode 194 may have a "D" shaped cross section having a substantially planar active surface 300. In this embodiment, electrode 194 is preferably fabricated from a solid wire that is ground or filed down similarly to the "C" shaped electrode configuration discussed above to form electrode edges 210. As shown in FIG. 15B, electrode 194 may also have a double slotted configuration that is generally formed by grinding both sides of a hollow tube. Alternatively, loop electrode 194 may be constructed from a formed wire (e.g., a round wire that has been drawn through a shaping die) shaped to create corners on the periphery of the extended loop electrode surface. FIGS. 16A–16E illustrate examples of electrode cross-sectional shapes that may be used with the present invention.

Figure 17A:
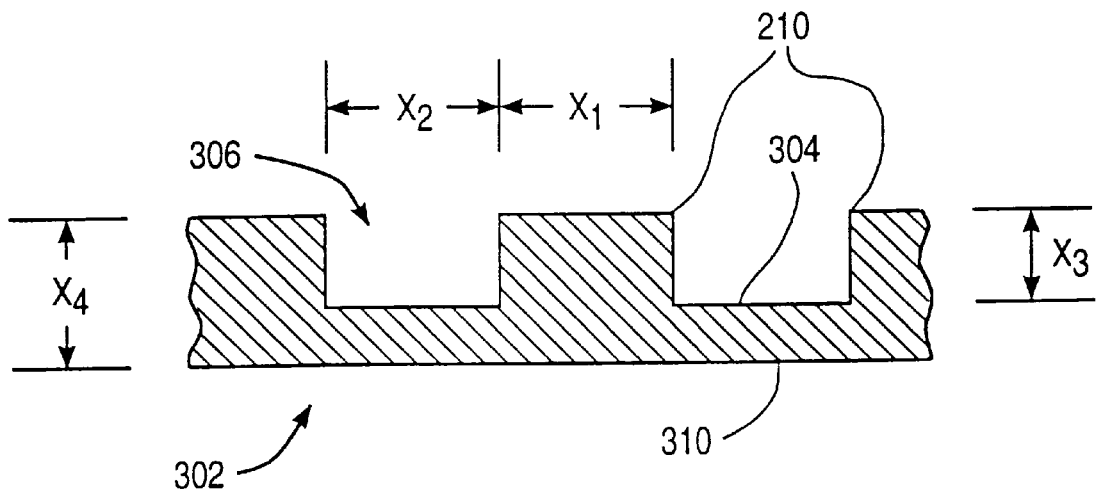
Figure 17B:
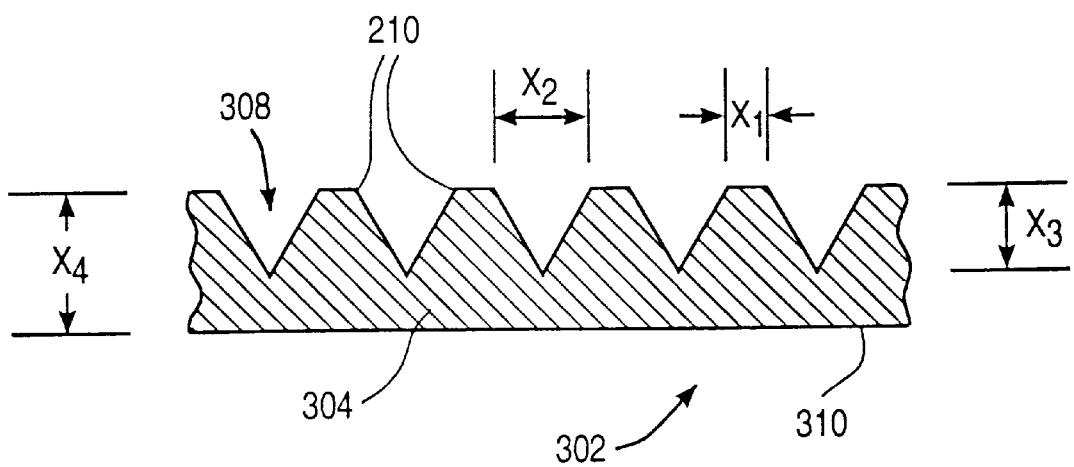
Figure 18A:
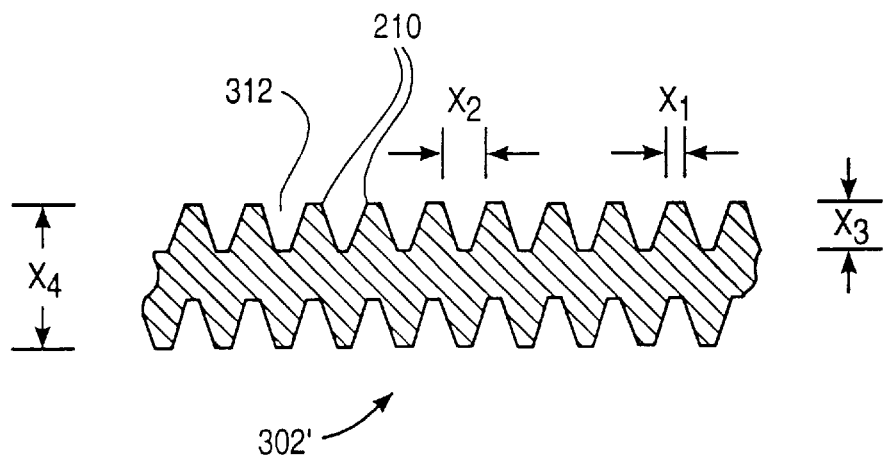

FIGS. 17A, 17B, 18A, 18B and 19 illustrate other alternatively shaped electrodes having transverse grooves or slots formed therein to promote high electric field intensities. Referring to FIGS. 17A and 17B, loop electrode 302 comprises an elongate body 304 having a plurality of spaced, transverse slots 306 (FIG. 17A) or grooves 308 (FIG. 17B) formed therein. The electrode edges 210 of slots 306 and grooves 308 will generally form the "active" portion of the electrode, while an opposing, substantially planar surface 310 forms the "non-active" portion of the electrode 302. An insulating layer (not shown) may be formed over surface 310 to prevent undesirable current flowing from this surface 310 to adjacent tissue. This allows the surgeon to selectively channel relatively high intensity electric fields towards the target site, while minimizing damage to non-target tissue surrounding the target site. Alternatively, electrode 302' may include grooves 312 on both sides so that both sides of electrode 302' are "active", as shown in FIG. 18A by virtue of the electrode edges 210 formed by the grooves or slots 312.

Figure 18B:
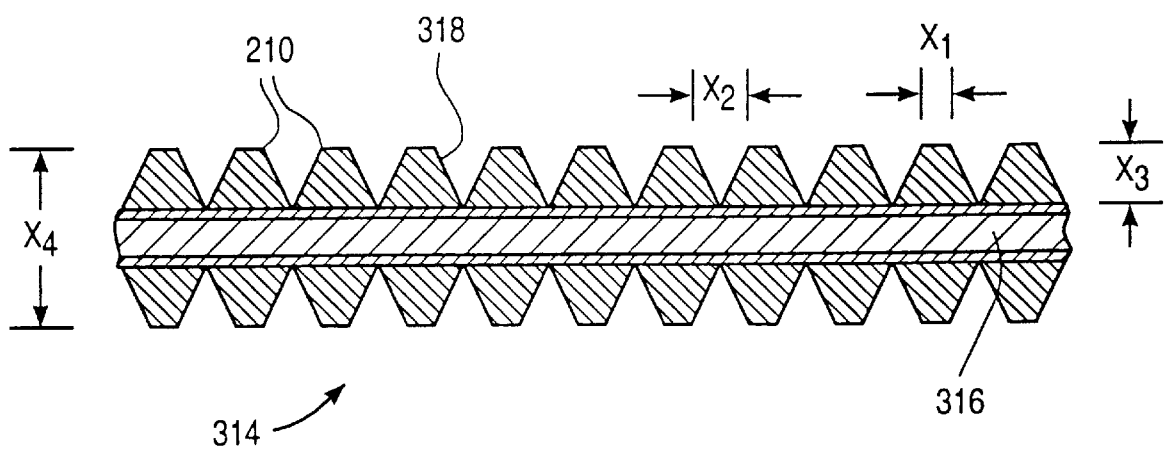

Referring to FIGS. 18B and 19, electrode 314 may have a "necklace" shape, in which electrode members are pre-shaped, perforated and then placed on an elongate support member (similar to beads on a necklace). Referring to FIG. 18B, one embodiment of electrode 314 includes an elongate support member 316, which may comprise an electrically conducting or insulating material, and a plurality of electrode disks 318 having an inner hole for receiving support member 316. Electrode disks 318 may be in contact with each other or longitudinally spaced from each other. In the latter configuration, support member 316 will be electrically conducting to electrically connect the disks 318 with each other. Referring to FIG. 19, each electrode disk 318 may be separated from each other by an insulating spacer 320. In this embodiment, the electrodes 318 may be electrically isolated from each other so that current limiting elements can be utilized to minimize undesirable current flow into surrounding fluids, as described above.

FIGS. 20A and 20B illustrate further alternative embodiments of the loop electrode according to the present invention. As shown in FIG. 20A, a formed wire has been shaped (e.g., by a shaping die) to form a "V" shape electrode 330. Since the ends 331, 332 of the "V" will promote high electric field intensities, they will preferably face in the cutting direction. In addition, an insulating layer 334 is formed onto the backside 335 of the "V". Similarly, FIG. 20B illustrates a "C" shaped electrode 336 having ends 337, 338 facing the cutting direction and an insulating layer 340 cover an opposite side 342 of electrode 336.

As shown in FIGS. 8A and 9, resecting loop electrode 194 is aligned with a plane forming an obtuse angle with the longitudinal axis of shaft 180. The obtuse angle is usually about 110 to 170 degrees, preferably about 120 to 150 degrees. During tissue resection, applicant has found that this orientation significantly facilitates initiating the requisite conditions for forming the vapor layer and inducing the discharge of energy therefrom. In this orientation, a greater fraction of loop electrode 194 is in direct contact with the tissue so that a greater fraction of the applied energy is directed to the tissue to be resected and a greater length of the resection loop is employed to cut the same depth of tissue. Thus, the duration of electrode contact with tissue is at least 30%, and usually at least 40%, greater at the 120° to 150° orientation than at the 90° orientation (see FIG. 15). This results in improved hemostasis of the resected tissue because there is more time to seal transected blood vessels with each pass of the resecting loop. In addition, a smaller fraction of loop electrode 194 is exposed to electrically conducting fluid surrounding the tissue, which minimizes undesirable current flow through this fluid.

Figure 22:
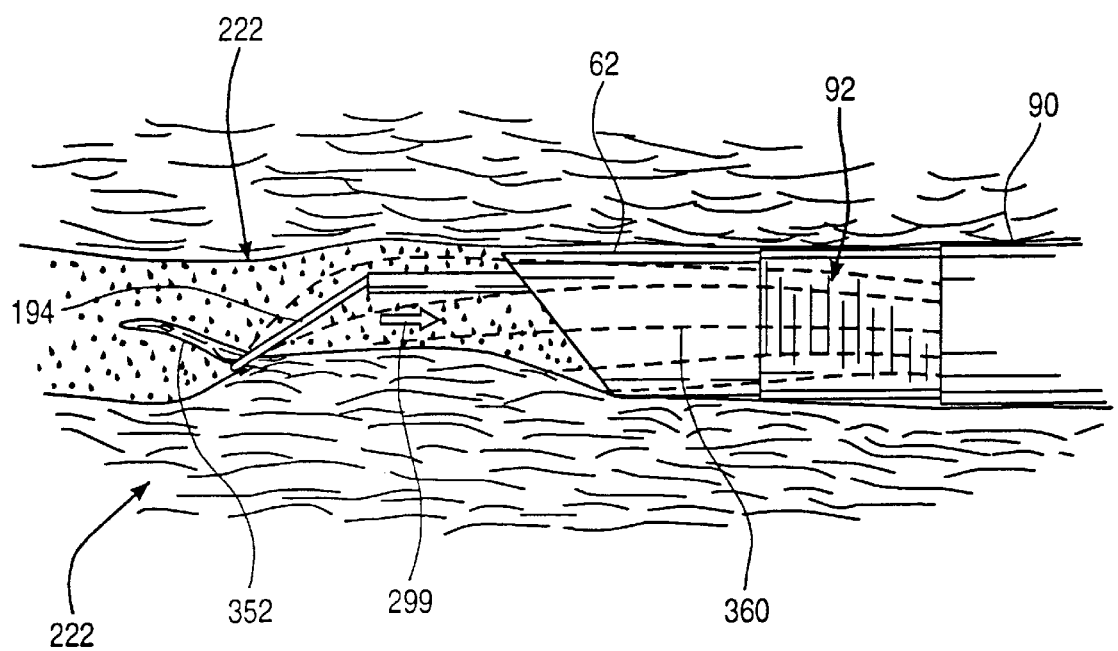
FIG. 22 is an enlarged view illustrating the resection of a prostate tissue portion with the resecting loop electrode of the present invention.

Referring now to FIGS. 21 and 22, a method for applying electrical energy to a target tissue in the patient's body will now be described. In particular, an exemplary procedure for treating an enlarged prostate 222 with electrosurgical system 11 will be described. Introducing sheath 60, return electrode oversheath 16, resecting loop assembly 112 are introduced transurethrally to the urethra 226 within prostate 222. In the monopolar mode, return electrode oversheath 16 will not be introduced, and a dispersive electrode (not shown) will be externally attached to the patient's skin. While viewing the region via telescope eyepiece 154, voltage can be applied from power supply 28 (see FIG. 1) between resecting loop electrode 194 and the exposed portion 92 of return electrode 16. Preferably, the applied voltage levels will be above about 500 volts (peak-to-peak). The cutting and resection of prostatic tissue 222 is achieved by engaging resecting loop electrode 194 against the prostatic tissue or positioning loop electrode 194 in close proximity to the prostatic tissue while simultaneously applying voltage from power supply 28 and axially displacing loop electrode 194 towards the distal end of introducing sheath 60 as illustrated by resection vector 299 in FIG. 22.

To complete the current path between the exposed portion 92 of the return electrode and resecting loop electrode 194, electrically conducting irrigant (e.g., isotonic saline) will preferably be delivered from liquid supply 21 through connector 160 along a liquid path between return electrode oversheath 16 and tubular shaft 62 to the target site. Alternatively, the site may already be submerged in liquid (e.g., arthroscopic procedures), or the liquid may be delivered through another instrument. The electrically conducting liquid provides a pathway for electrical current flow between prostatic tissue 222 and return electrode 92, as illustrated by the current flux lines 360 in FIG. 22. When a voltage difference is applied between loop electrode 194 and return electrode 92, high electric field intensities will be generated at the shaped edges 210 of electrode 194 to cause ablation of tissue 222.

Referring now to FIG. 22, the design of the surface geometry of resecting loop electrode 194 promotes high current densities at the surface of electrode 194, especially at the shaped edges. In contrast, the current density decreases rapidly with distance from the surface of resecting loop 194. Since the extent of the exposed portion 92 of return electrode will be about 2 to 4 cm, the surface area of exposed portion 92 will be about 5 to 10 cm². In contrast, the surface area of the resecting loop electrode 194 is about 0.003 cm². As a result, the current density at the return electrode 92 is 1,700 to 3,400 times smaller than at the resecting loop 194 resulting in current density levels below the threshold of injury to living tissue.

The surgeon can usually effect an efficient cutting motion by simultaneously coagulating smaller vessels transected during the resection of the tissue (see FIG. 22). There may, however, be occasions during the resection of tissue in which larger blood vessels are transected and do not become simultaneously sealed (coagulated) by the higher current densities which surround loop electrode 194. In such situations, resecting loop electrode 194 may be used specifically for coagulating and sealing of a transected blood vessel by engaging the tissue at the locus of the bleeding vessel and lightly applying pressure while simultaneously applying a lower voltage level, i.e., a voltage level which is below the threshold of effecting cutting or resection of tissue. Typically, an applied voltage level of less than 500 volts (peak-to-peak), preferably less than 400 volts (peak-to-peak) will be sufficient to effect coagulation of transected blood vessels without cutting or resection of tissue. This dual mode of operation of resecting loop 112 is preferably accomplished by providing dual footpedal 37, which includes a cutting mode pedal 39 and a coagulation mode pedal 38. Alternatively, the dual mode may be carried out with voltage control buttons 30.

During the course of the tissue resection procedure, telescopic lumen 152 (FIG. 21) and the attached return electrode oversheath 16 can be withdrawn from introducing sheath 160 of resectoscope 10 by releasing a mechanical locking member 350. Following the withdrawal of the working elements of resectoscope 10, the open lumen of introducing sheath 60 can be used to remove the "chip-shaped" tissue portions 352 (FIG. 22) formed during the resection process.

Figure 23:
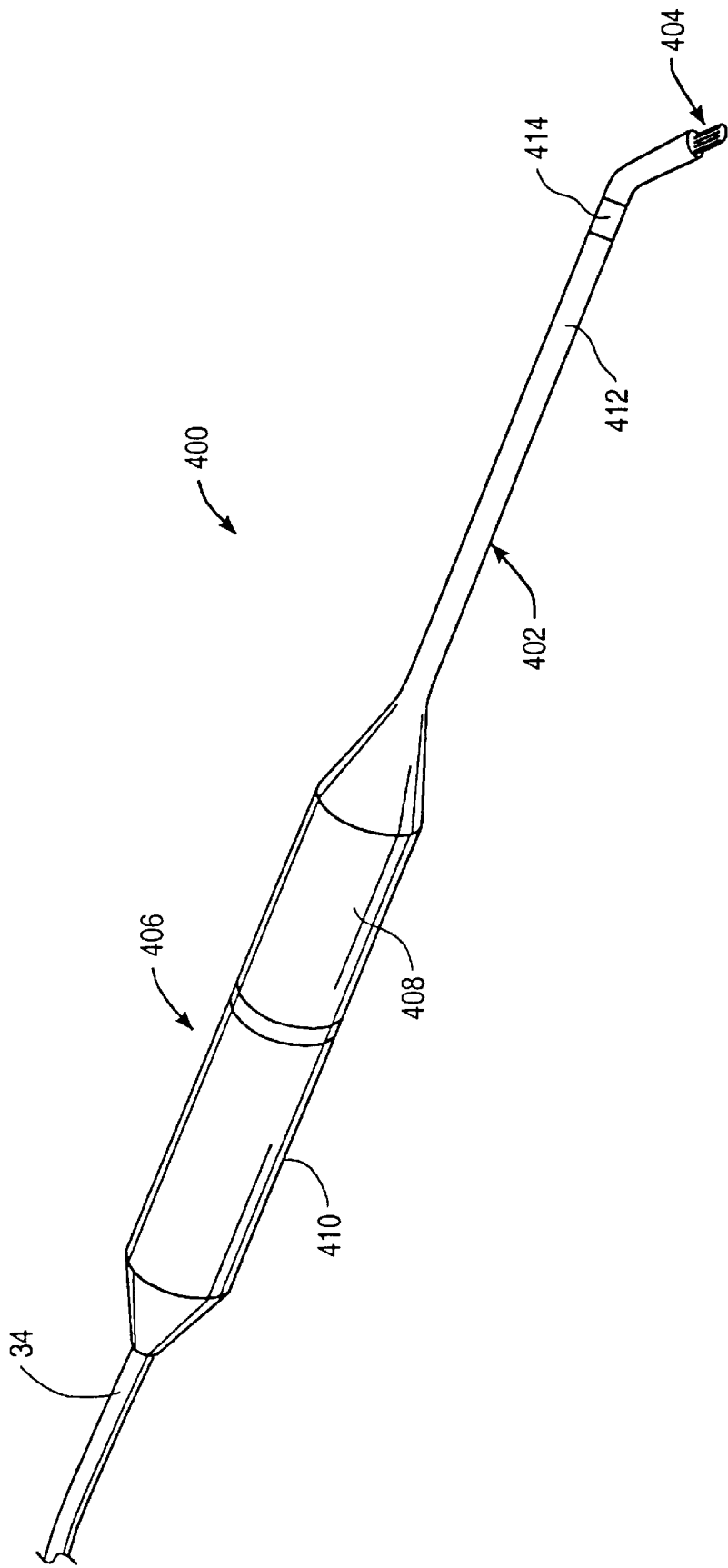
FIG. 23 illustrates a planar ablation probe for ablating tissue in confined spaces within a patient's body according to the present invention.

Referring to FIGS. 23–32, preferred systems and methods for ablating tissue in confined (e.g., narrow) body spaces will now be described. FIG. 23 illustrates an exemplary planar ablation probe 400 according to the present invention. Similar to the resectoscope described above, probe 400 can be incorporated into electrosurgical system 11 (or other suitable systems) for operation in either the bipolar or monopolar modalities. Probe 400 generally includes a support member 402, a distal working end 404 attached to the distal end of support member 402 and a proximal handle 408 attached to the proximal end of support member 402. As shown in FIG. 23, handle 406 includes a handpiece 408 and a power source connector 410 removably coupled to handpiece 408 for electrically connecting working end 404 with power supply 28 through cable 34 (see FIG. 1).

In the embodiment shown in FIG. 23, planar ablation probe 400 is configured to operate in the bipolar modality. Accordingly, support member 402 functions as the return electrode and comprises an electrically conducting material, such as titanium, or alloys containing one or more of nickel, chromium, iron, cobalt, copper, aluminum, platinum, molybdenum, tungsten, tantalum or carbon. In the preferred embodiment, support member 402 is an austenitic stainless steel alloy, such as stainless steel Type 304 from MicroGroup, Inc., Medway, Mass. As shown in FIG. 23, support member 402 is substantially covered by an insulating layer 412 to prevent electric current from damaging surrounding tissue. An exposed portion 414 of support member 402 functions as the return electrode for probe 400. Exposed portion 414 is preferably spaced proximally from active electrodes 416 by a distance of about 1 to 20 mm.

Figure 24:
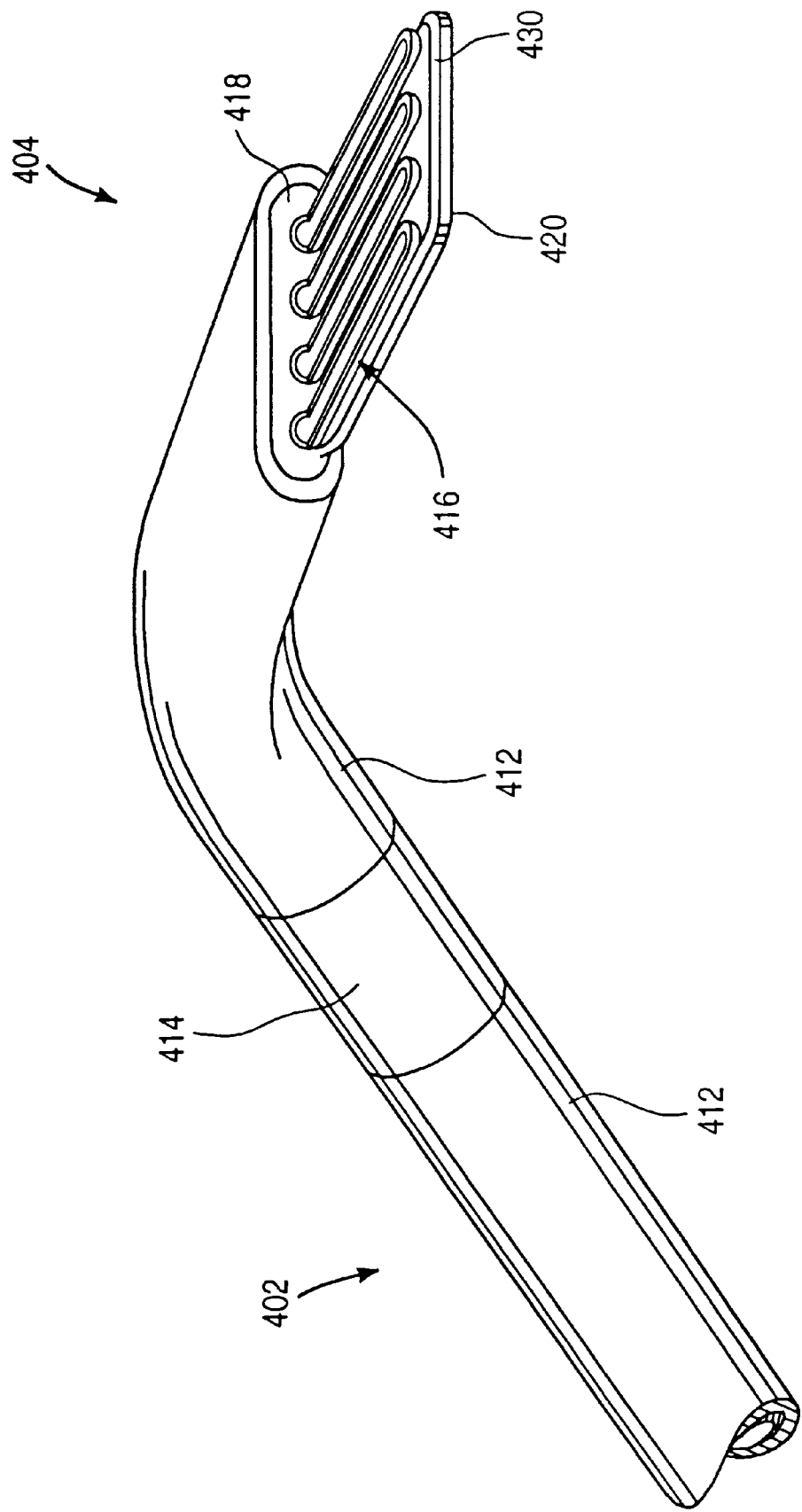
FIG. 24 illustrates a distal portion of the planar ablation probe of FIG. 23.
Figure 25A:
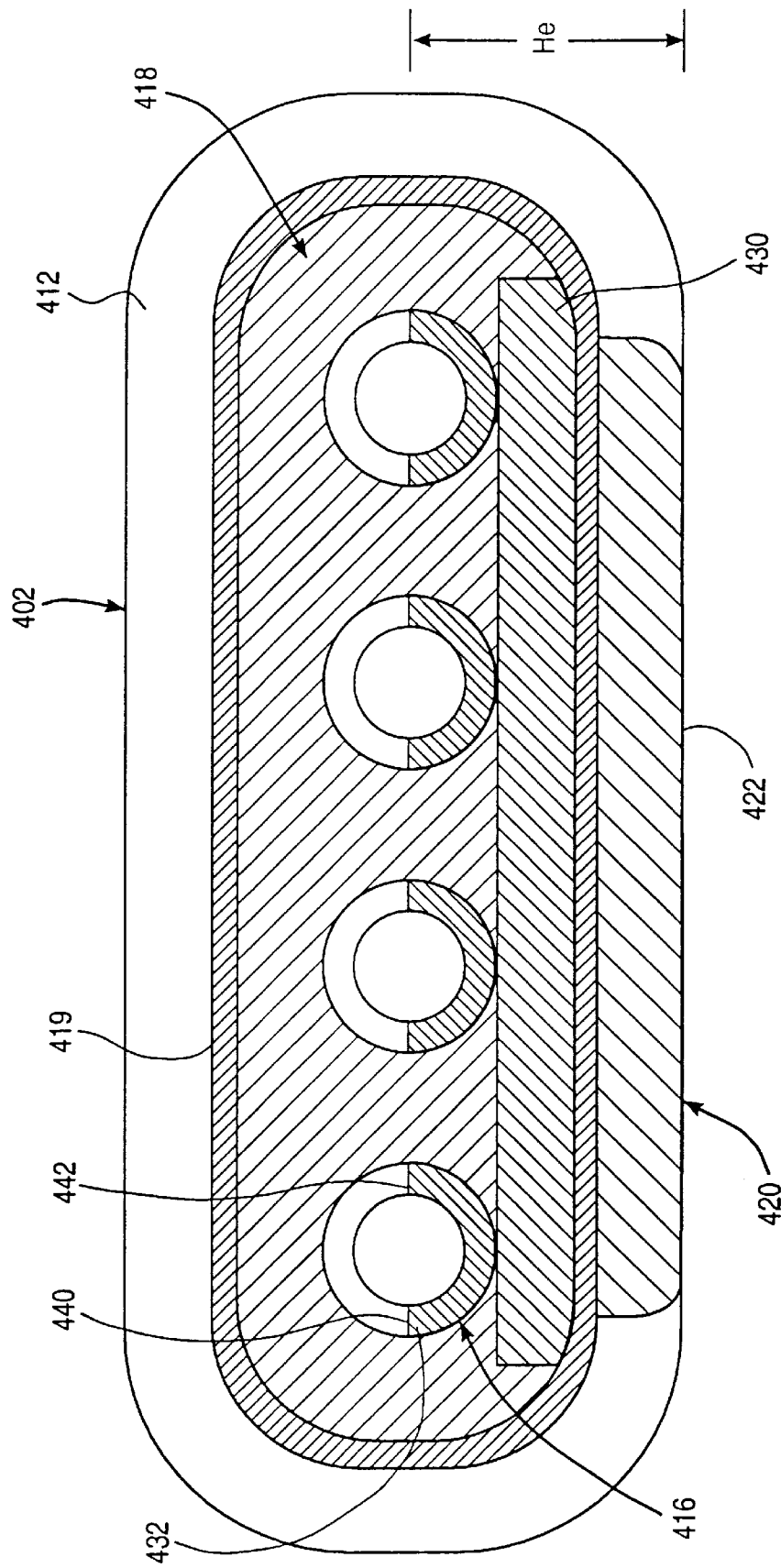
FIG. 25A is a front sectional view of the planar ablation probe, illustrating an array of semi-cylindrical active electrodes.

Referring to FIGS. 24 and 25, planar ablation probe 400 further comprises a plurality of active electrodes 416 extending from an electrically insulating spacer 418 at the distal end of support member 402. Of course, it will be recognized that probe 400 may include a single electrode depending on the size of the target tissue to be treated and the accessibility of the treatment site (see FIG. 30, for example). Insulating spacer 418 is preferably bonded to support member 402 with a suitable epoxy adhesive 419 to form a mechanical bond and a fluid-tight seal. Electrodes 416 usually extend about 2.0 mm to 20 mm from spacer 418, and preferably less than 10 mm. A support tongue 420 extends from the distal end of support member 402 to support active electrodes 416. Support tongue 420 and active electrodes 416 have a substantially low profile to facilitate accessing narrow spaces within the patient's body, such as the spaces between adjacent vertebrae and between articular cartilage and the meniscus in the patient's knee. Accordingly, tongue 420 and electrodes 416 have a substantially planar profile, usually having a combined height He of less than 4.0 mm, preferably less than 2.0 mm and more preferably less than 1.0 mm (see FIG. 25). In the case of ablation of meniscus near articular cartilage, the height He of both the tongue 420 and electrodes 416 is preferably between about 0.5 to 1.5 mm. The width of electrodes 416 and support tongue 420 will usually be less than 10.0 mm and preferably between about 2.0 to 4.0 mm.

Support tongue 420 includes a "non-active" surface 422 opposing active electrodes 416 covered with an electrically insulating layer (not shown) to minimize undesirable current flow into adjacent tissue or fluids. Non-active surface 422 is preferably atraumatic, i.e., having a smooth planar surface with rounded corners, to minimize unwanted injury to tissue in contact therewith, such as articular cartilage, as the working end of probe 400 is introduced into a narrow, confined body space. Non-active surface 422 of tongue 420 help to minimize iatrogenic injuries to tissue, such as articular cartilage, so that working end 404 of probe 400 can safely access confined spaces within the patient's body.

Figure 25B:
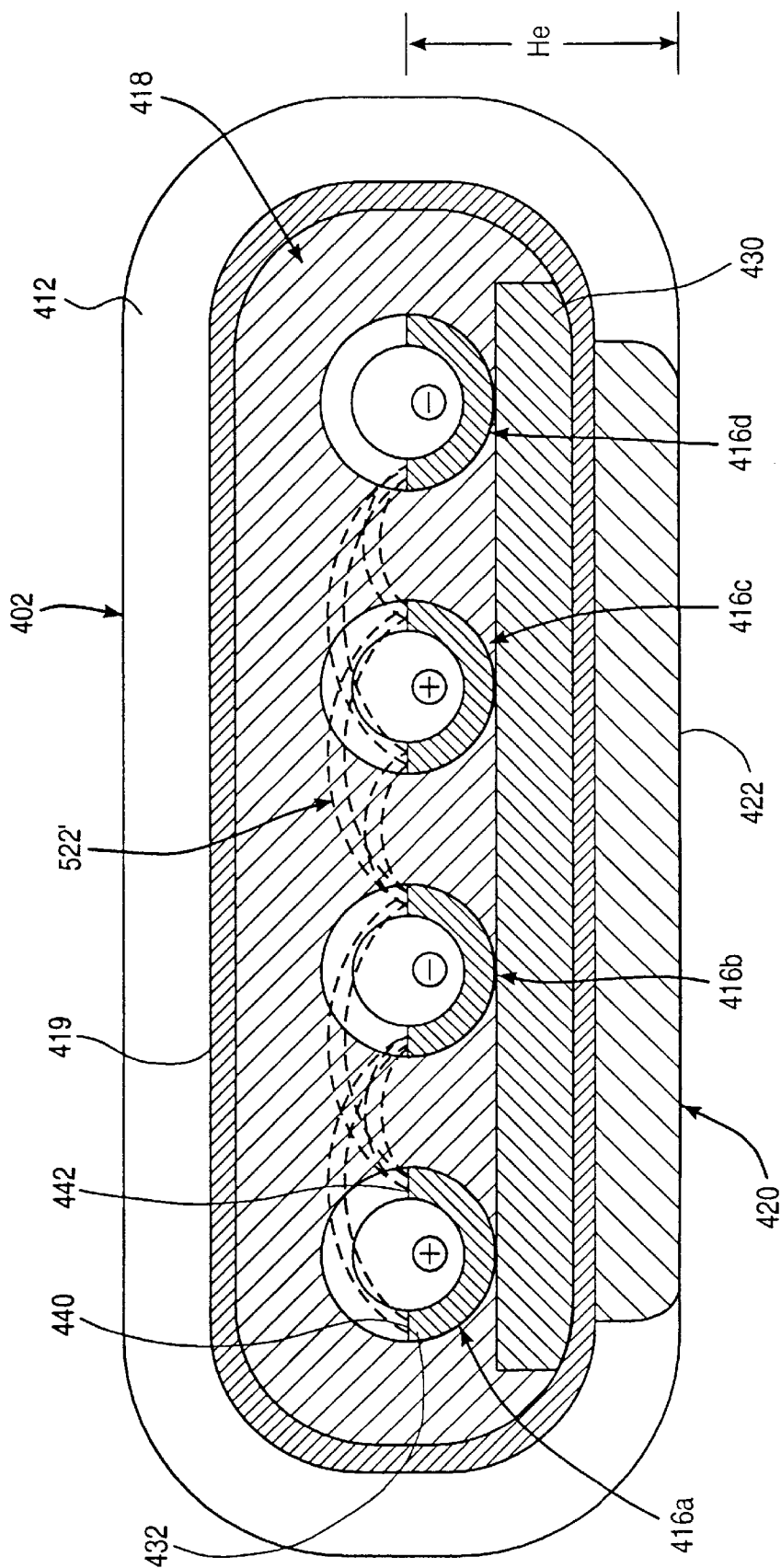
FIG. 25B is a front sectional view of an alternative planar ablation probe, illustrating an array of active electrodes having opposite polarities.
Figure 26:
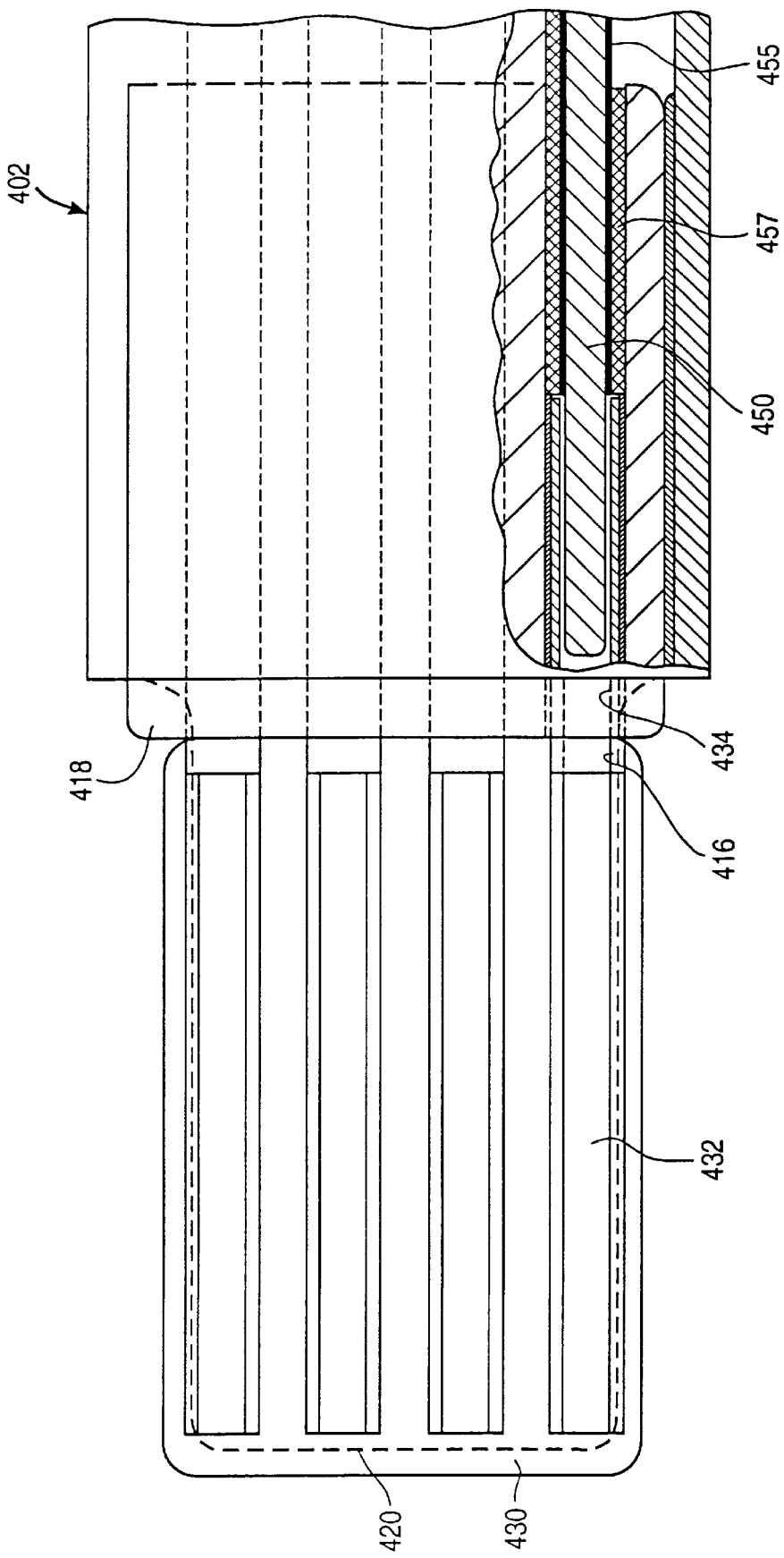
FIG. 26 is a top, partial section, view of the working end of the planar ablation probe of FIG. 23.

Referring to FIGS. 25 and 26, an electrically insulating support member 430 is disposed between support tongue 420 and active electrodes 416 to inhibit or prevent electric current from flowing into tongue 420. Insulating member 430 and insulating layer 412 preferably comprise a ceramic, glass or glass ceramic material, such as alumina. Insulating member 430 is mechanically bonded to support tongue 420 with a suitable epoxy adhesive to electrically insulate active electrodes 416 from tongue 420. As shown in FIG. 26, insulating member 430 may overhang support tongue 420 to increase the electrical path length between the active electrodes 416 and the insulation covered support tongue 420.

Figure 27:
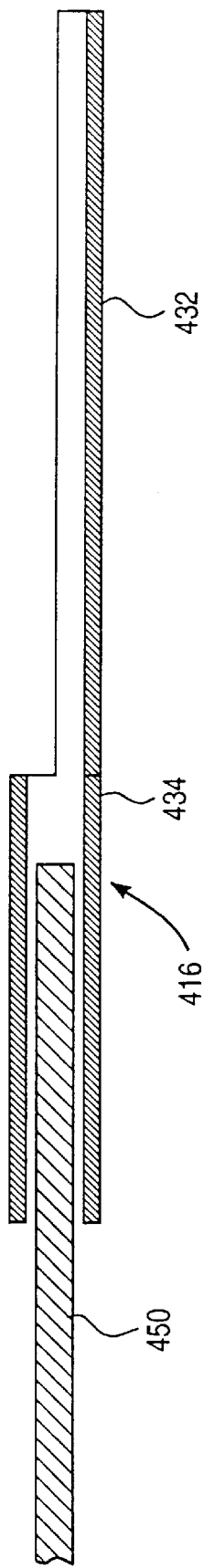
FIG. 27 is a side cross-sectional view of the working end of the planar ablation probe, illustrating the electrical connection with one of the active electrodes of FIG. 26.

As shown in FIGS. 25–27, active electrodes 416 are preferably constructed from a hollow, round tube, with at least the distal portion 432 of electrodes 416 being filed off to form a semi-cylindrical tube with first and second ends 440, 442 facing away from support tongue 420. Preferably, the proximal portion 434 of electrodes 416 will remain cylindrical to facilitate the formation of a crimp-type electrical connection between active electrodes 416 and lead wires 450 (see FIG. 27). As shown in FIG. 26, cylindrical proximal portions 434 of electrodes 416 extend beyond spacer 418 by a slight distance of 0.1 mm to 0.4 mm. The semi-cylindrical configuration of distal electrode portion 432 increases the electric field intensity and associated current density around the edges of ends 440, 442, as discussed above. Alternatively, active electrodes 416 may have any of the shapes and configurations described above or other configurations, such as square wires, triangular shaped wires, U-shaped or channel shaped wires and the like. In addition, the surface of active electrodes 416 may be roughened, e.g., by grit blasting, chemical or electrochemical etching, to further increase the electric field intensity and associated current density around distal portions 432 of electrodes 416.

Figure 28:
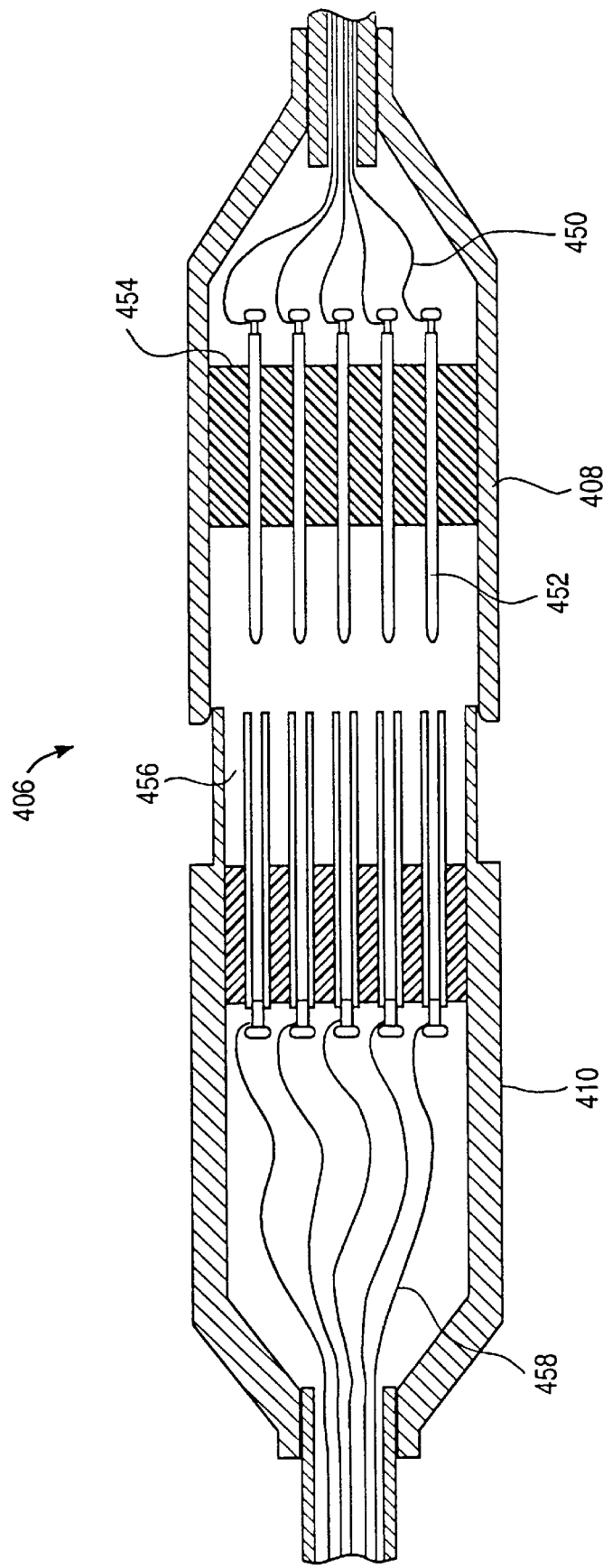
FIG. 28 is a side cross-sectional view of the proximal end of the planar ablation probe, illustrating the electrical connection with a power source connector.

As shown in FIG. 28, each lead wire 450 terminates at a connector pin 452 contained in a pin insulator block 454 within handpiece 408. Lead wires 450 are covered with an insulation layer (not shown), e.g., Tefzel™, and sealed from the inner portion of support member 402 with an adhesive seal 457 (FIG. 26). In the preferred embodiment, each electrode 416 is coupled to a separate source of voltage within power supply 28. To that end, connector pins 452 are removably coupled to mating receptacles 456 within connector 410 to provide electrical communication with active electrodes 416 and power supply 28 (FIG. 1). Electrically insulated lead wires 458 connect receptacles 456 to the corresponding sources of voltage within power supply 28. The electrically conductive wall 414 of support member 402 serves as the return electrode, and is suitably coupled to one of the lead wires 450.

In an alternative embodiment, adjacent electrodes 416 may be connected to the opposite polarity of source 28 so that current flows between adjacent active electrodes 416 rather than between active electrodes 416 and return electrode 414. By way of example, FIG. 25B illustrates a distal portion of a planar ablation probe 400' in which electrodes 416a and 416c are at one voltage polarity (i.e., positive) and electrodes 416b and 416d are at the opposite voltage polarity (negative). When a high frequency voltage is applied between electrodes 416a, 416c and electrodes 416b, 416d in the presence of electrically conducting liquid, current flows between electrodes 416a, 416c and 416b, 416d as illustrated by current flux lines 522'. Similar to the above embodiments, the opposite surface 420 of working end 404' of probe 400' is generally atraumatic and electrically insulated from active electrodes 416a, 416b, 416c and 416d to minimize unwanted injury to tissue in contact therewith.

In an exemplary configuration, each source of voltage includes a current limiting element or circuitry (not shown) to provide independent current limiting based on the impedance between each individual electrode 416 and return electrode 414. The current limiting elements may be contained within the power supply 28, the lead wires 450, cable 34, handle 406, or within portions of the support member 402 distal to handle 406. By way of example, the current limiting elements may include resistors, capacitors, inductors, or a combination thereof. Alternatively, the current limiting function may be performed by (1) a current sensing circuit which causes the interruption of current flow if the current flow to the electrode exceeds a predetermined value and/or (2) an impedance sensing circuit which causes the interruption of current flow (or reduces the applied voltage to zero) if the measured impedance is below a predetermined value. In another embodiment, two or more of the electrodes 416 may be connected to a single lead wire 450 such that all of the electrodes 416 are always at the same applied voltage relative to return electrode 414. Accordingly, any current limiting elements or circuits will modulate the current supplied or the voltage applied to the array of electrodes 416, rather than limiting their current individually, as discussed in the previous embodiment.

Referring to FIGS. 29–32, methods for ablating tissue structures with planar ablation probe 400 according to the present invention will now be described. In particular, exemplary methods for treating a diseased meniscus within the knee (FIGS. 29–31) and for removing soft tissue between adjacent vertebrae in the spine (FIG. 32) will be described. In both procedures, at least the working end 404 of planar ablation probe 400 is introduced to a treatment site either by minimally invasive techniques or open surgery. Electrically conducting liquid is delivered to the treatment site, and voltage is applied from power supply 28 between active electrodes 416 and return electrode 414. The voltage is preferably sufficient to generate electric field intensities near active electrodes that form a vapor layer in the electrically conducting liquid, and induce the discharge of energy from the vapor layer to ablate tissue at the treatment site, as described in detail above.

Figure 29:
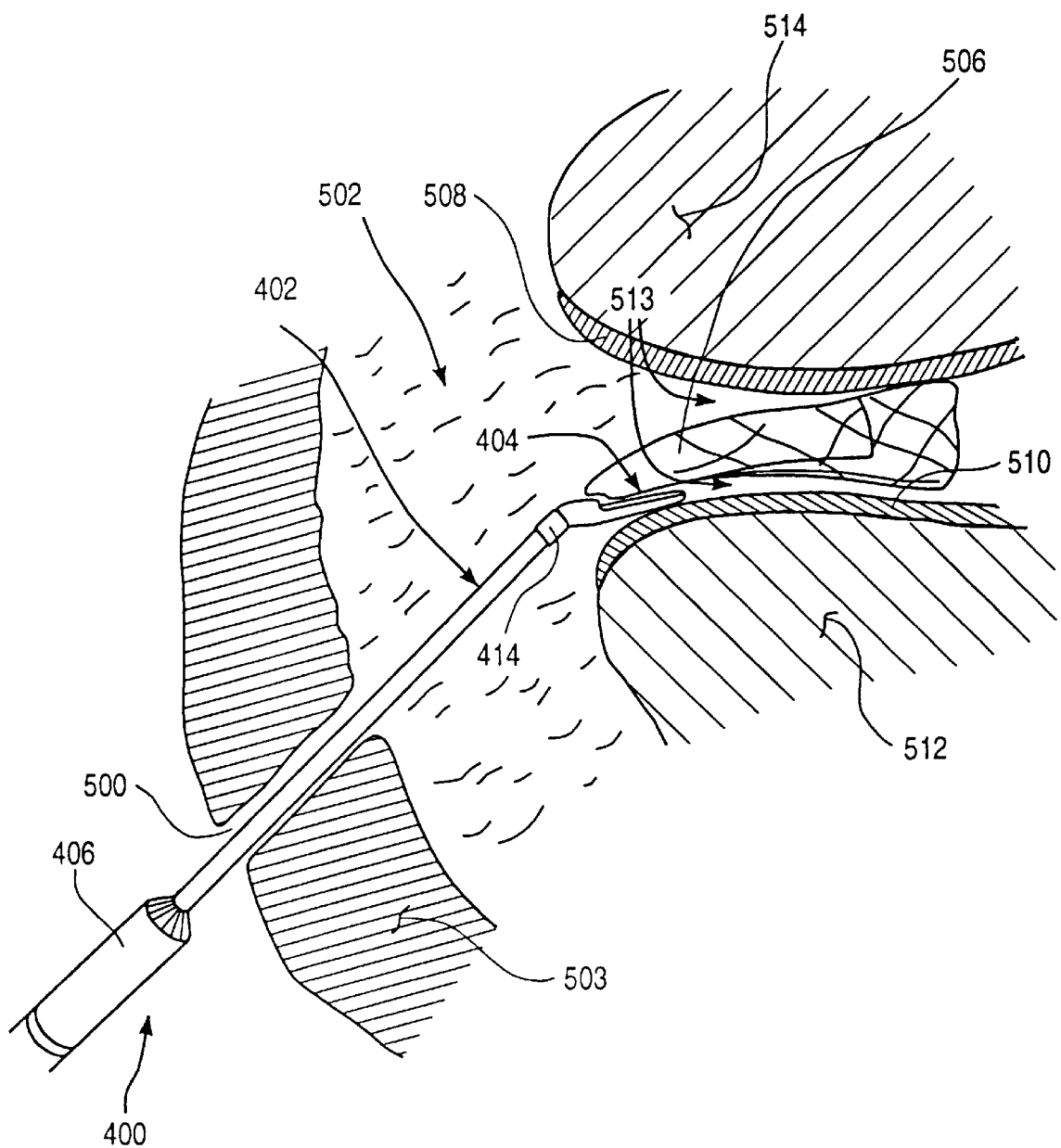
FIG. 29 is a schematic view illustrating the ablation of meniscus tissue located close to articular cartilage between the tibia and femur of a patient with the ablation probe of FIG. 23.

Referring to FIG. 29, working end 404 and at least the distal portion of support member 402 are introduced through a percutaneous penetration 500, such as a cannula, into the arthroscopic cavity 502. The insertion of probe 400 is usually guided by an arthroscope (not shown) which includes a light source and a video camera to allow the surgeon to selectively visualize a zone within the knee joint. To maintain a clear field of view and to facilitate the generation of a vapor layer, a transparent, electrically conductive irrigant 503, such as isotonic saline, is injected into the treatment site either through a liquid passage in support member 402 of probe 400, or through another instrument. Suitable methods for delivering irrigant to a treatment site are described in commonly assigned, co-pending application Ser. No. 08/485,219, filed on Jun. 7, 1995 (Attorney Docket 16238-000600), the complete disclosure of which has previously been incorporated herein by reference.

In the example shown in FIG. 29, the target tissue is a portion of the meniscus 506 adjacent to and in close proximity with the articular cartilage 510, 508 which normally covers the end surfaces of the tibia 512 and the femur 514, respectively. The articular cartilage 508, 510 is important to the normal functioning of joints, and once damaged, the body is generally not capable of regenerating this critical lining of the joints. Consequently, it is desirable that the surgeon exercise extreme care when treating the nearby meniscus 506 to avoid unwanted damage to the articular cartilage 508, 510. The confined spaces 513 between articular cartilage 508, 510 and meniscus 506 within the knee joint are relatively narrow, typically on the order of about 1.0 mm to 5.0 mm. Accordingly, the narrow, low profile working end 404 of ablation probe 400 is ideally suited for introduction into these confined spaces 513 to the treatment site. As mentioned previously, the substantially planar arrangement of electrodes 416 and support tongue 420 (typically having a combined height of about 0.5 to 1.5 mm) allows the surgeon to deliver working end 404 of probe 400 into the confined spaces 513, while minimizing contact with the articular cartilage 508, 510 (see FIG. 30).

Figure 30:
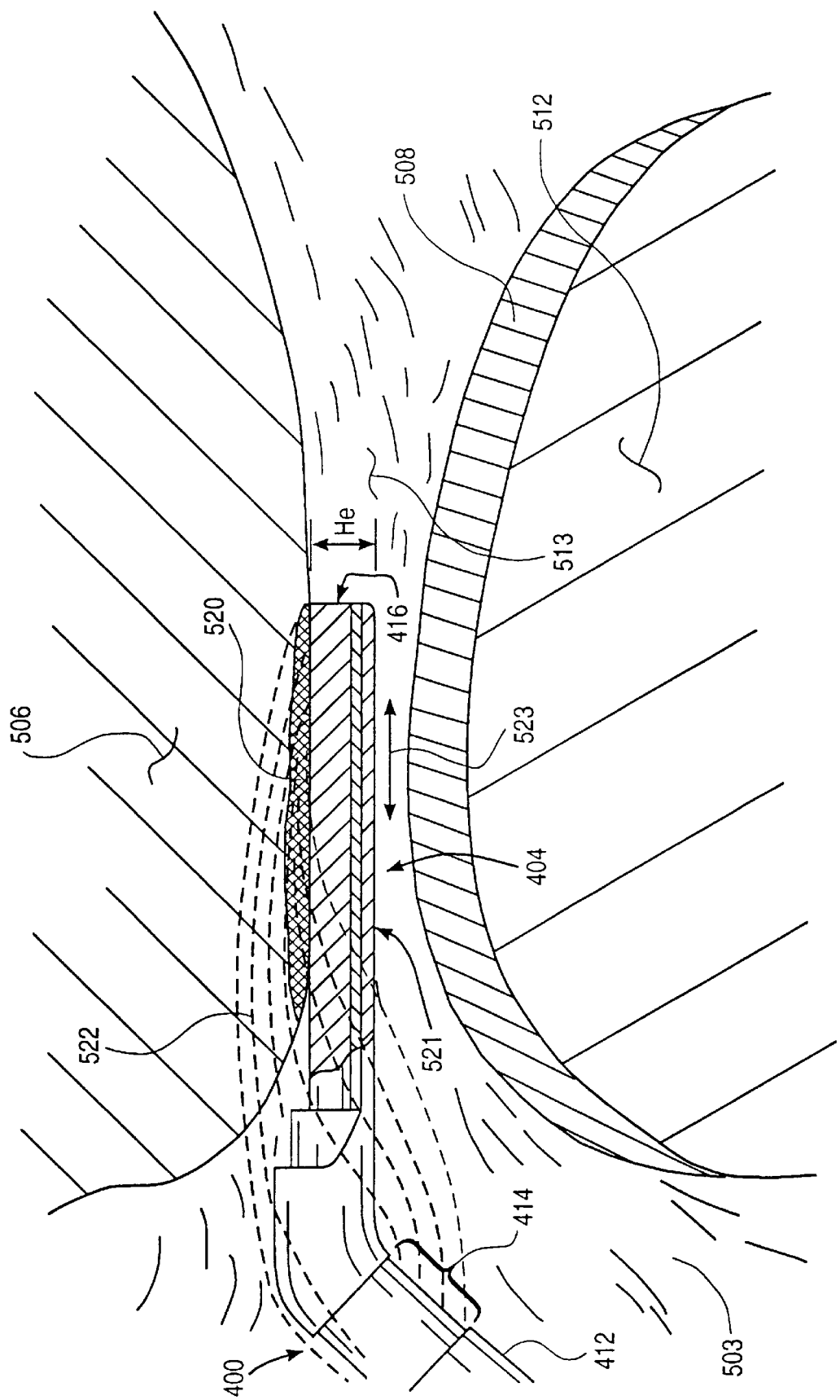
FIG. 30 is an enlarged view of the distal portion of the planar ablation probe, illustrating ablation or cutting of meniscus tissue.

As shown in FIG. 30, active electrodes 416 are disposed on one face of working end 404 of probe 400. Accordingly, a zone 520 of high electric field intensity is generated on each electrode 416 on one face of working end 404 while the opposite side 521 of working end 404 is atraumatic with respect to tissue. In addition, the opposite side 521 is insulated from electrodes 416 to minimize electric current from passing through this side 521 to the tissue (i.e., adjacent articular cartilage 508). As shown in FIG. 30, the bipolar arrangement of active electrodes 416 and return electrode 414 causes electric current to flow along flux lines 522 predominantly through the electrically conducting irrigant 503, which envelops the tissue and working end 404 of ablation probe 400 and provides an electrically conducting path between electrodes 416 and return electrode 414. As electrodes 416 are engaged with, or positioned in close proximity to, the target meniscus 506, the high electric field present at the electrode edges cause controlled ablation of the tissue by forming a vapor layer and inducing the discharge of energy therefrom. In addition, the motion of electrodes 416 relative to the meniscus 506 (as shown by vector 523) causes tissue to be removed in a controlled manner. The presence of the irrigant also serves to minimize the increase in the temperature of the meniscus during the ablation process because the irrigant generally comes in contact with the treated tissue shortly after one of the electrodes 416 has been translated across the surface of the tissue.

Figure 32:
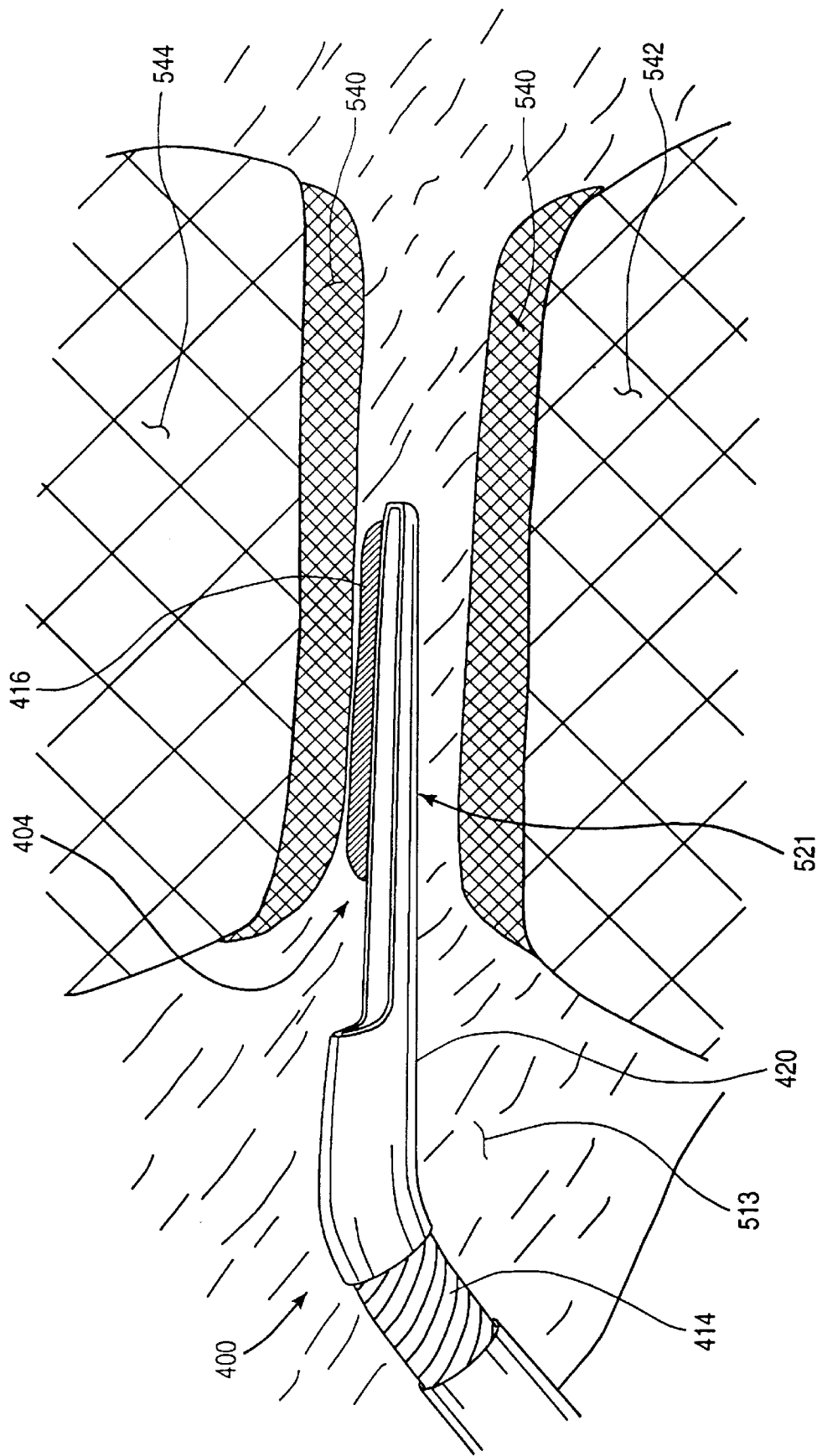
FIG. 32 is a schematic view illustrating the ablation of soft tissue from adjacent surfaces of the vertebrae with the planar ablation probe of the present invention.

Referring now to FIG. 32, an exemplary method for removing soft tissue 540 from the surfaces of adjacent vertebrae 542, 544 in the spine will now be described. Removal of this soft tissue 540 is often necessary, for example, in surgical procedures for fusing or joining adjacent vertebrae together. Following the removal of tissue 540, the adjacent vertebrae 542, 544 are stabilized to allow for subsequent fusion together to form a single monolithic vertebra. As shown, the low-profile of working end 404 of probe 400 (i.e., thickness values as low as 0.2 mm) allows access to and surface preparation of closely spaced vertebrae. In addition, the shaped electrodes 416 promote substantially high electric field intensities and associated current densities between active electrodes 416 and return electrode 414 to allow for the efficient removal of tissue attached to the surface of bone without significantly damaging the underlying bone. The "non-active" insulating side 521 of working end 404 also minimizes the generation of electric fields on this side 521 to reduce ablation of the adjacent vertebra 542.

The target tissue is generally not completely immersed in electrically conductive liquid during surgical procedures within the spine, such as the removal of soft tissue described above. Accordingly, electrically conducting liquid will preferably be delivered into the confined spaces 513 between adjacent vertebrae 542, 544 during this procedure. The fluid may be delivered through a liquid passage (not shown) within support member 402 of probe 400, or through another suitable liquid supply instrument.

Figure 31:
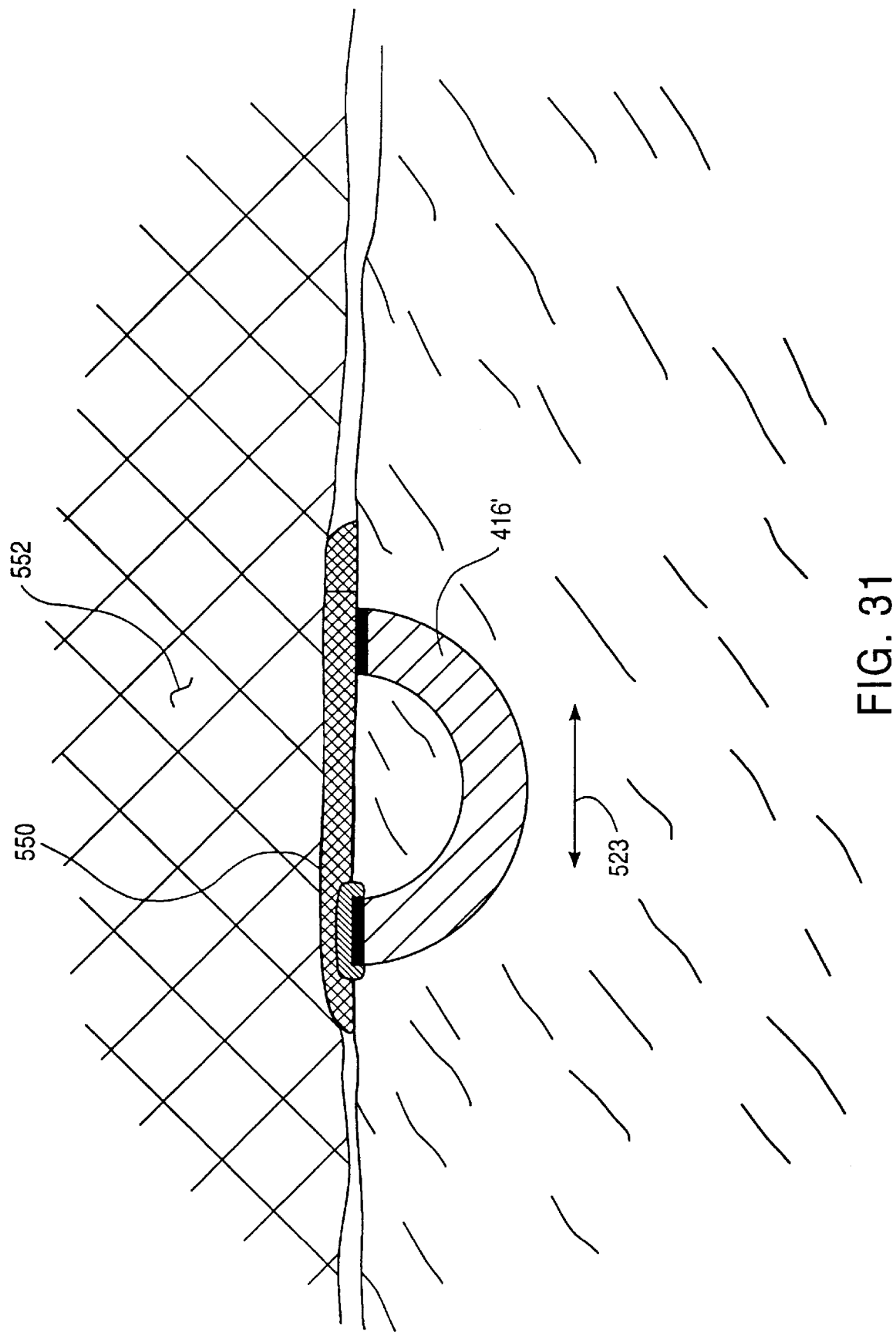
FIG. 31 illustrates a method of ablating tissue with a planar ablation probe incorporating a single active electrode.

Other modifications and variations can be made to disclose embodiments without departing from the subject invention as defined in the following claims. For example, it should be clearly understood that the planar ablation probe 400 described above may incorporate a single active electrode, rather than a plurality of such active electrodes as described above in the exemplary embodiment. FIG. 31 illustrates a portion of a planar ablation probe according to the present invention that incorporates a single active electrode 416' for generating high electric field densities 550 to ablate a target tissue 552. Electrode 416' may extend directly from a proximal support member, as depicted in FIG. 31, or it may be supported on an underlying support tongue (not shown) as described in the previous embodiment. As shown, the representative single active electrode 416' has a semicylindrical cross-section, similar to the electrodes 416 described above. However, the single electrode 416' may also incorporate any of the above described configurations (e.g., square or star shaped solid wire) or other specialized configurations depending on the function of the device.

Figure 33A:
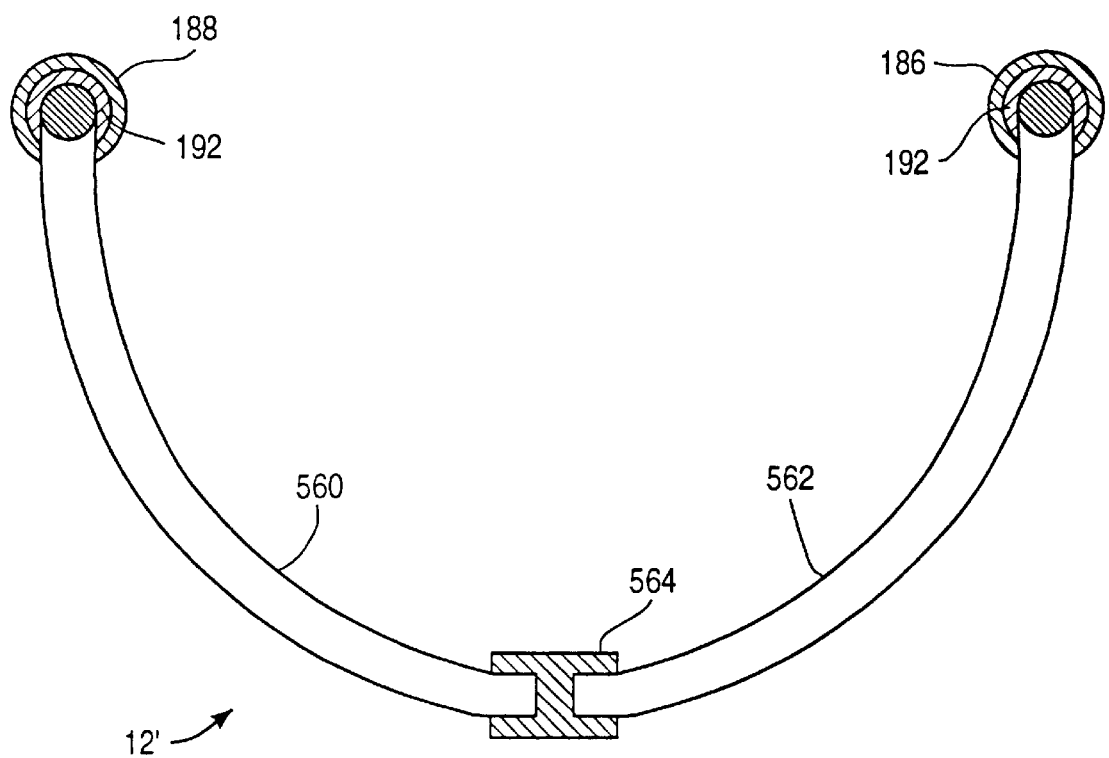
FIGS. 33A–33E illustrate another embodiment of the resecting loop electrode incorporating two active electrodes.
Figure 33B:
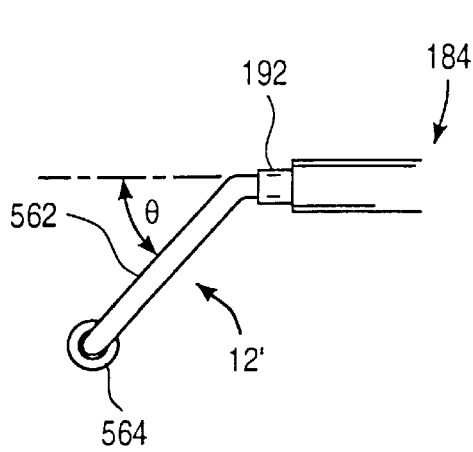
Figure 33C:
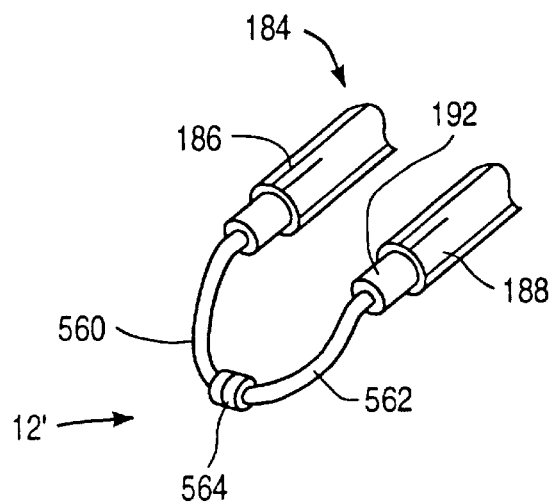
Figure 33D:
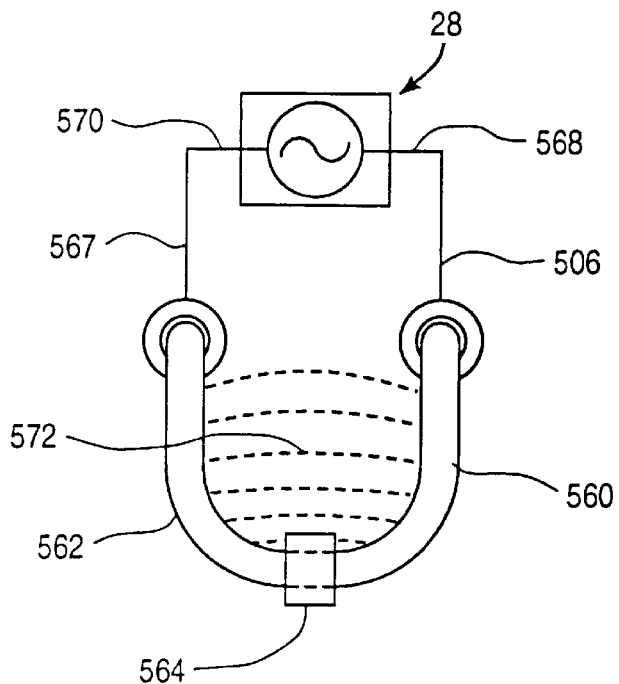
Figure 33E:
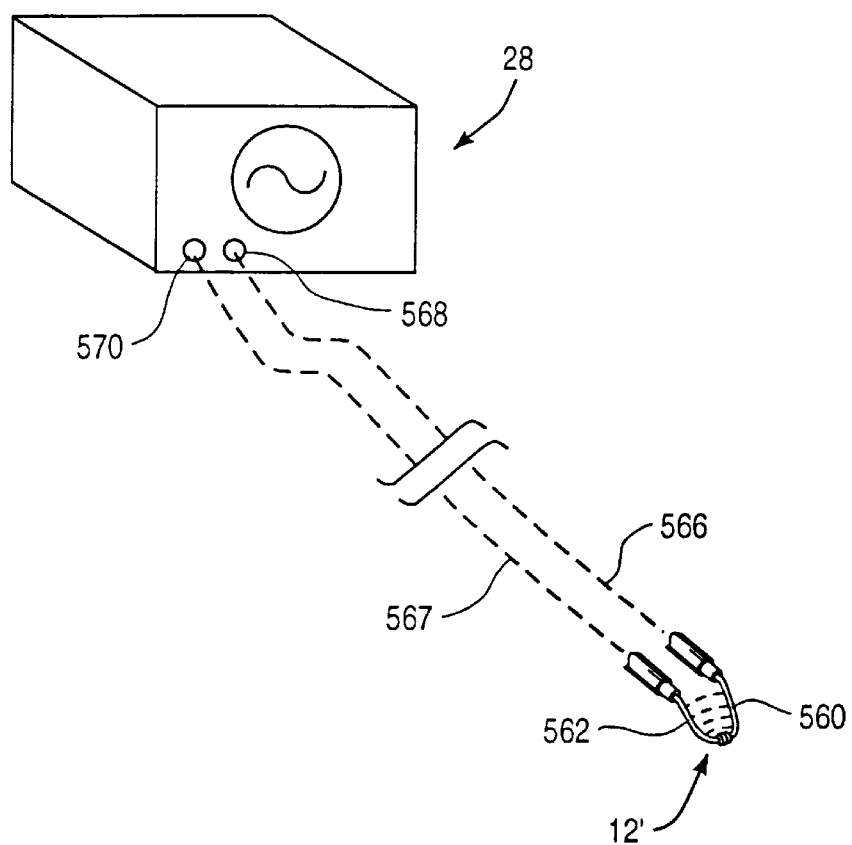

FIGS. 33A–33E illustrate another embodiment of a resecting loop assembly 12' incorporating two electrodes 560, 562 which are electrically isolated from direct contact with each other by an insulating spacer 564. Electrodes 560, 562 may comprise solid wires, hollow tubes, or any of the cross-sectional shapes and configurations discussed above to afford regions of high electric field intensity. Similar to the above embodiments, the proximal ends of electrodes 560, 562 extend from electrically insulating tubular members 192, which extend from hollow arms 186, 188 of a bifurcated support member 184. As shown in FIGS. 33D and 33E, electrodes 560, 562 are each connected to an electrically conducting lead 566, 567 which, in turn, connect to first and second poles 568, 570, respectively, of the output of power supply 28. With this electrical arrangement, current (illustrated by current flux lines 572) flows between electrodes 560, 562 when a radiofrequency voltage difference is applied between poles 568, 570 of power supply 28. The current effects tissue cutting ablation, shrinkage and/or coagulation in these regions within electrodes 560, 562. A return electrode is not utilized in this arrangement and, therefore, return electrode oversheath 16 is not necessary.

Figure 34A:
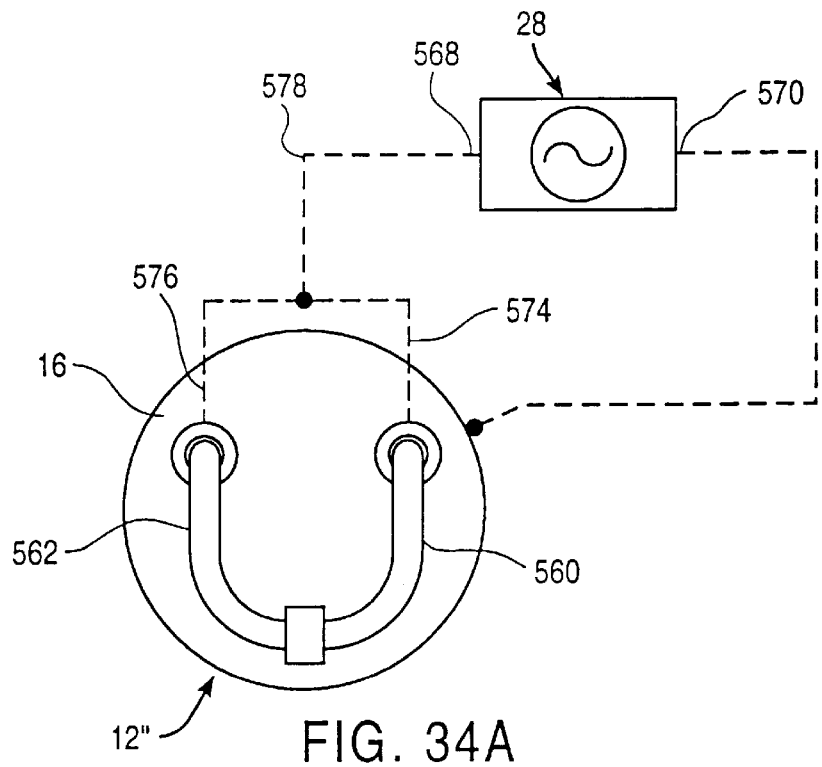
FIGS. 34A and 34B illustrate a resecting loop electrode incorporating two active electrodes connected to a common lead.
Figure 34B:
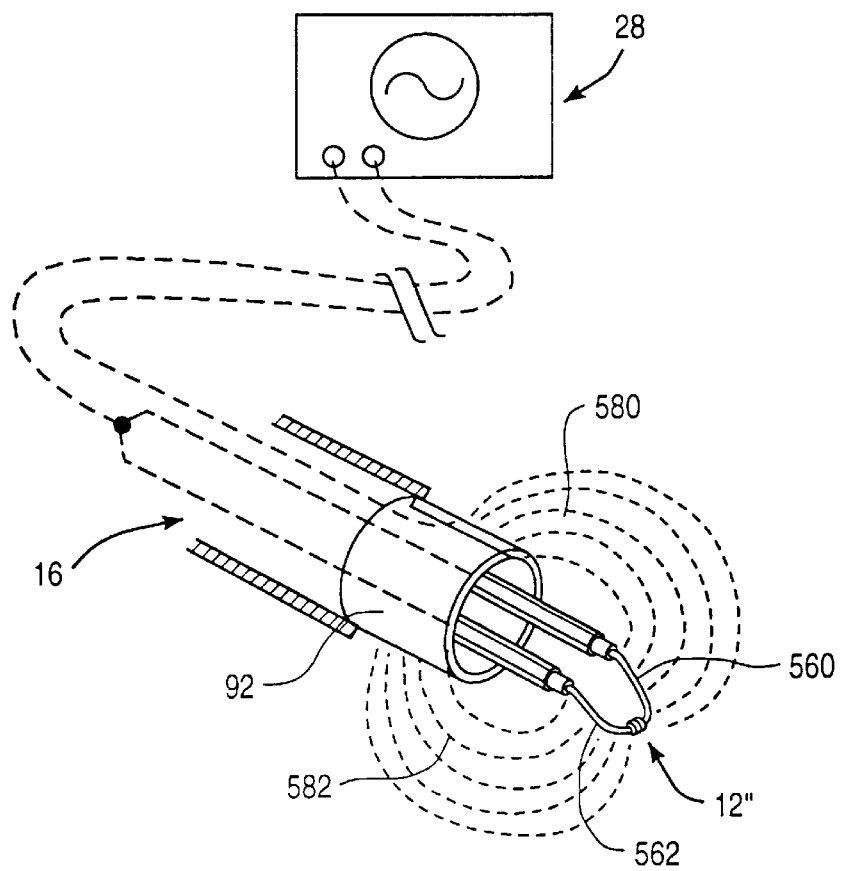

FIGS. 34A and 34B illustrate another embodiment of resecting loop assembly 12' in which electrodes 560, 562 are each connected to an electrically conducting lead wire 574, 576 which are connected to a common lead 578. The distal end of common lead 578 is connected to a first pole 568 of power supply. In this electrical arrangement, return electrode oversheath 16 (see FIG. 4) will be coupled to second pole 570 of power supply 28. Thus, when electrodes 560, 562 are in contact with tissue and/or electrically conducting fluid and an RF voltage difference is applied between poles 568, 570, electrical current flows independently between electrode 560 and return electrode 16 and between electrode 562 and return electrode 16 (as illustrated by current flux lines 580, 582, respectively).

Figure 35A:
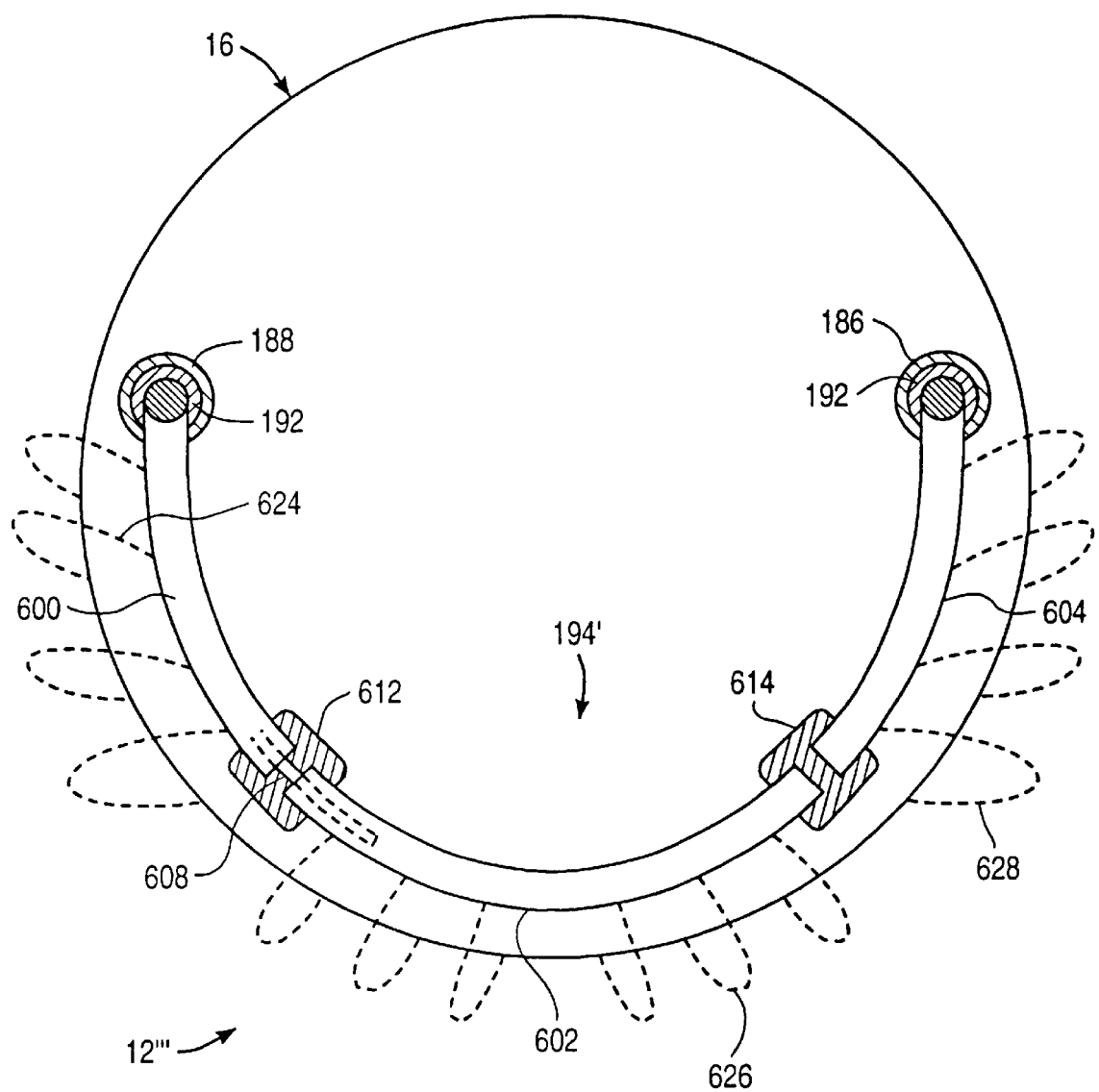
FIGS. 35A and 35B illustrate a resecting loop electrode with three active electrodes.
Figure 35B:
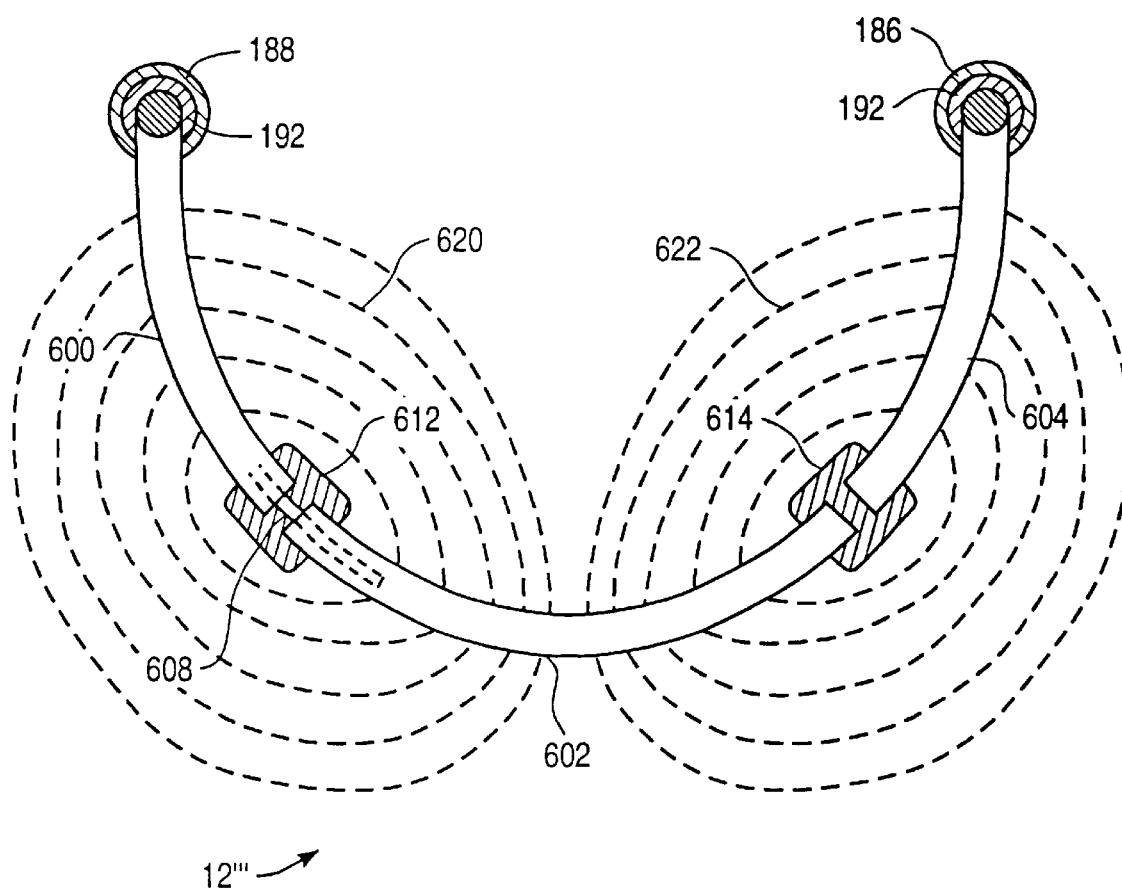

FIGS. 35A and 35B illustrate yet another embodiment of resecting loop assembly 12''' incorporating three electrodes 600, 602, 604 assembled to form loop electrode 194'. Lead wires electrically couple electrodes 600, 602, 604 to power supply 28. One of the lead wires 608 extends through, and is electrically insulated from, electrode 600, as shown in FIG. 35B. Electrodes 600-604 are mechanically spaced and electrically insulated from each other by insulating spacers 612, 614. Similar to previous embodiments, electrodes 600 and 604 extend from electrically insulating tubular members 192, which extend from hollow arms 186, 188 of a bifurcated support member 184.

FIG. 35B illustrates the current flux lines 620, 622 for one electrical arrangement for connected electrodes 600-604 to power supply 28. In this arrangement, electrodes 600, 604 are connected to first pole 568 of power supply 28 (see FIGS. 34D and 34E) in a manner similar to that described above for resecting loop assembly 12' and electrode 602 is coupled to second pole 570 of power supply 28 (i.e., return electrode 16 is not utilized in this arrangement). When electrodes 600-604 are in contact with tissue and/or electrically conducting liquid and an RF voltage difference is applied between poles 568, 570, electrical current flows between electrodes 600 and 602 and between electrodes 604 and 602, as illustrated by current flux lines 620, 622, respectively.

FIG. 35A illustrates the current flux lines 624, 626, 628 for another electrical arrangement for resecting loop assembly 12'''. In this arrangement, electrodes 600, 602 and 604 are independently connected to first pole 568 of power supply 28 and return electrode 16 is coupled to second pole 570 (see FIGS. 34A and 34B). As shown, current flows independently between each electrode 600, 602 and 604 and exposed portion 92 of return electrode 16.

As will be evident to those skilled in the art, the foregoing example of resecting loop assembly 12''' can be extended to configurations having four or more electrodes.

Figure 36:
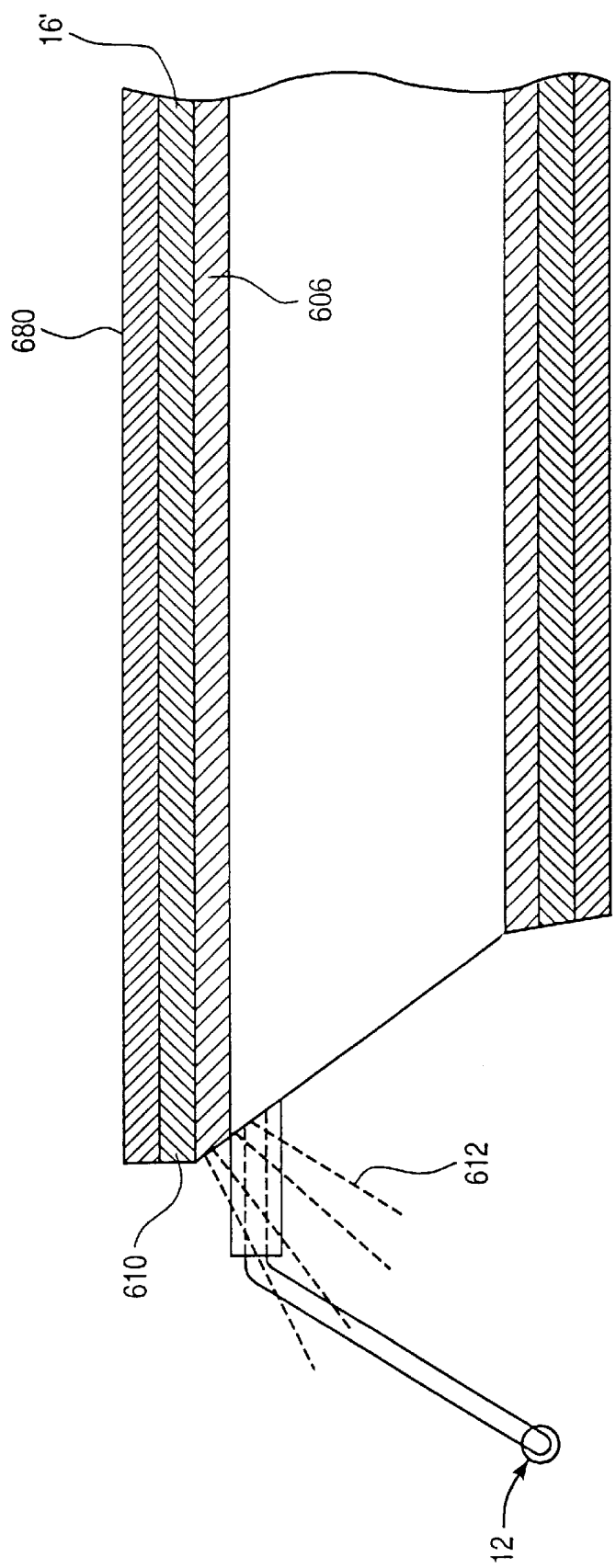
FIG. 36 is a partial side cross-section of an alternative embodiment of the return electrode oversheath of FIG. 4.

FIG. 36 illustrates another embodiment of electrosurgical system 11 in which the return electrode sheath 16' is completely covered with inner and outer insulating layers 606, 680 except for an exposed portion 610 at the distal end of the sheath 16' that extends beyond the inner insulating layer 606. The exposed portion 610 generates a current flow path 612 between the resecting loop electrode 12 and the return electrode 16'. If return electrode 16' is used in conjunction with and positioned over an insulated resecting loop shaft (not shown), the return electrode oversheath 16' will be insulated on its outer surface only. Alternatively, the sheath of the resectoscope can be replaced with a sheath having the insulation features and return electrode arrangement shown in FIG. 36 such that an additional overshaft return electrode is not required.

What is claimed is:

1. An electrosurgical probe for applying electrical energy to a target site within a confined spaced in a patient's body, the instrument comprising:

a shaft having a proximal end portion and a distal end portion extending from the shaft, the distal end portion having an axial length, a thickness substantially less than said length and a width substantially larger than said thickness to form a substantially planar body having an active side and a non-active side opposing the active side sized to fit within a relatively narrow space within the patient's body;

an insulating member extending alone the non-active side of the substantially planar body;

at least one active electrode extending along the active side of the substantially planar body of the distal end portion of the shaft and being insulated from the non-active side and having an exposed surface area;

a return electrode having an exposed surface area larger than the exposed surface area of the active electrode and being spaced from the active electrode; and a connector disposed near the proximal end portion of the shaft for electrically coupling the active electrode to a high frequency voltage source.

2. The probe of claim 1 wherein the distal end portion of the shaft is configured for introduction into spaces between articular cartilage and the meniscus between the tibia and the femur to access meniscal tissue at the meniscus/tibial plateau interface.

3. The probe of claim 1 wherein the distal end portion of the shaft is configured for introduction into spaces between intervertebral disks in the spine.

4. The probe of claim 1 wherein the thickness of the distal end portion from the active side to the non-active side is less than 2 mm.

5. The probe of claim 1 wherein the thickness of the distal end portion from the active side to the non-active side is less than 1 mm.

6. An electrosurgical probe for applying electrical energy to a target site within a confined spaced in a patient's body, the instrument comprising:

a shaft having a proximal end portion, a distal end portion extending from the shaft and a middle portion coupling the proximal and distal end portions, the middle portion having a thickness, the distal end portion having an axial length, a thickness substantially less than said length and substantially less than the thickness of the middle portion and a width substantially larger than said thickness of the distal end portion to form a substantially planar body having an active side and a non-active side opposing the active side sized to fit within a relatively narrow space within the patient's body;

at least one active electrode disposed on the active side of the distal end portion of the shaft and being insulated from the non-active side; and a connector disposed near the proximal end portion of the shaft for electrically coupling the electrode to a high frequency voltage source.

7. The probe of claim 6 wherein the distal end portion includes a substantially planar support member underlying and insulated from the active electrode.

8. The probe of claim 7 wherein the support member has a substantially smooth, atraumatic surface opposite the active electrode to minimize damage to tissue.

9. The probe of claim 6 further comprising a return electrode positioned proximally to the active electrode for generating a current return path therebetween.

10. The probe of claim 9 wherein the return electrode is located on the shaft.

11. The probe of claim 6 wherein the active electrode comprises an elongate body having a distal active portion with a surface geometry configured to promote substantially high electric field intensities between the active portion and the target site when a high frequency voltage is applied to the electrode.

12. The probe of claim 11 wherein the active portion of the active electrode defines a semi-circular transverse cross-sectional shape with first and second ends and an inner slot therebetween, the first and second ends each having a pair of edges for promoting localized high electric field intensities near the edges.

13. The probe of claim 12 wherein the distal end portion of the shaft includes a support member and an insulating layer disposed between the support member and the active electrode, the first and second ends of the active portion facing away from the insulating layer.

14. The probe of claim 13 wherein the first and second ends of the active portion form a planar surface that is substantially parallel to the support member.

15. The probe of claim 11 wherein the active portion of the active electrode is positioned in close proximity to the target site in the presence of electrically conducting liquid, the surface geometry of the active portion configured to promote high electric field intensities sufficient to vaporize the electrically conducting liquid in a thin layer over at least a portion of the electrode surface and to induce the discharge of energy from the vapor layer.

16. The probe of claim 6 wherein the distal end portion of the shaft has a length less than about 10 mm and a width less than about 10 mm.

17. The probe of claim 6 further comprising an array of electrically isolated active electrodes, each having a semi-circular cross-section with first and second ends and an inner slot therebetween, the first and second ends each having a pair of edges for promoting localized high electric field intensities near the edges.

18. The probe of claim 17 wherein the active electrodes are spaced from each other by a distance of about 5 to 100 mils.

* * * * *